United States Patent
Hasegawa

(10) Patent No.: US 9,808,316 B2
(45) Date of Patent: Nov. 7, 2017

(54) MEDICAL APPARATUS RACK

(71) Applicant: Terumo Kabushiki Kaisha, Tokyo (JP)

(72) Inventor: Makoto Hasegawa, Fujinomiya (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 234 days.

(21) Appl. No.: 14/521,212

(22) Filed: Oct. 22, 2014

(65) Prior Publication Data
US 2015/0041419 A1 Feb. 12, 2015

Related U.S. Application Data

(63) Continuation of application No. PCT/JP2013/061654, filed on Apr. 19, 2013.

(30) Foreign Application Priority Data

Apr. 23, 2012 (JP) .................. 2012-098033

(51) Int. Cl.
A61M 5/14 (2006.01)
F16M 13/02 (2006.01)
(Continued)

(52) U.S. Cl.
CPC .......... A61B 19/0256 (2013.01); A61B 50/20 (2016.02); A61B 50/22 (2016.02);
(Continued)

(58) Field of Classification Search
CPC ...... A61B 50/20; A61B 50/22; A61M 5/1415; A61M 5/1413; A61M 5/1417; A61M 5/1418; F16M 13/022
See application file for complete search history.

(56) References Cited

U.S. PATENT DOCUMENTS 4,338,485 A * 7/1982 Fullenkamp ........... A47B 79/00
174/501
4,607,897 A * 8/1986 Schwartz ............... F16M 11/42
248/188.7
(Continued)

FOREIGN PATENT DOCUMENTS

GB WO 2012065649 * 5/2012
JP 09-131301 A 5/1997
(Continued)

OTHER PUBLICATIONS

International Search Report dated May 28, 2013 issued in Application No. PCT/JP2013/061654.
(Continued)

Primary Examiner — Leslie A Nicholson, III
Assistant Examiner — Kimberley S Wright
(74) Attorney, Agent, or Firm — Foley & Lardner LLP

(57) ABSTRACT

A medical device rack in which a medical device is detachably mountable, the medical device rack including: a main body; and a mounting section provided in the main body, the mounting section being configured such that the medical device is detachably mountable in a posture oriented in a lateral direction. The mounting section includes a supporting portion configured to be detachably fitted to the medical device to support the medical device in a rotatable manner.

20 Claims, 24 Drawing Sheets

(51) Int. Cl.
*A61M 5/142* (2006.01)
*A61B 19/02* (2006.01)
*A61M 5/145* (2006.01)
*F16M 11/04* (2006.01)
*F16M 11/22* (2006.01)
*A61B 50/22* (2016.01)
*A61B 50/20* (2016.01)

(52) U.S. Cl.
CPC ........ *A61M 5/1413* (2013.01); *A61M 5/1415* (2013.01); *A61M 5/1452* (2013.01); *A61M 5/1458* (2013.01); *F16M 11/041* (2013.01); *F16M 11/22* (2013.01); *A61M 2205/502* (2013.01); *A61M 2209/08* (2013.01)

(56) References Cited

U.S. PATENT DOCUMENTS

| | | | | |
|---|---|---|---|---|
| 4,662,524 | A * | 5/1987 | Fullenkamp | A47B 57/565 211/190 |
| 4,700,922 | A | 10/1987 | Gross | |
| 4,898,578 | A * | 2/1990 | Rubalcaba, Jr. | A61M 5/172 128/DIG. 13 |
| 5,186,337 | A * | 2/1993 | Foster | A61G 13/107 174/493 |
| 5,284,255 | A * | 2/1994 | Foster | A61G 13/107 174/493 |
| 5,452,807 | A * | 9/1995 | Foster | A61G 13/107 211/168 |
| 5,647,491 | A | 7/1997 | Foster et al. | |
| 5,755,691 | A * | 5/1998 | Hilborne | A61M 5/142 417/474 |
| 5,829,723 | A * | 11/1998 | Brunner | A61M 5/1413 248/222.13 |
| 6,407,335 | B1 | 6/2002 | Franklin-Lees et al. | |
| 6,593,528 | B2 * | 7/2003 | Franklin-Lees | A61M 5/1413 174/50 |
| 7,546,993 | B1 | 6/2009 | Walker | |
| 7,884,735 | B2 * | 2/2011 | Newkirk | A61G 7/012 211/26 |
| 8,512,300 | B1 * | 8/2013 | Sacchetti | A61G 7/0503 340/573.7 |
| 8,617,137 | B1 * | 12/2013 | Sacchetti | A61G 7/0503 5/617 |
| 2003/0204330 | A1 * | 10/2003 | Allgeyer | A61B 5/0059 702/32 |
| 2004/0164220 | A1 * | 8/2004 | Newkirk | A61B 50/10 248/647 |
| 2005/0096593 | A1 * | 5/2005 | Pope | A61M 5/1452 604/122 |
| 2006/0179571 | A1 * | 8/2006 | Newkirk | A61G 7/012 5/600 |
| 2007/0219495 | A1 * | 9/2007 | Kato | A61M 5/1413 604/131 |
| 2008/0272254 | A1 | 11/2008 | Harr et al. | |
| 2010/0252702 | A1 * | 10/2010 | Spang, Jr. | A61M 39/283 248/219.4 |
| 2013/0272773 | A1 * | 10/2013 | Kamen | F16B 2/02 403/11 |
| 2014/0046296 | A1 * | 2/2014 | Clarke | A61M 5/1456 604/507 |
| 2014/0209550 | A1 * | 7/2014 | Pryor | A61M 5/1417 211/85.13 |
| 2014/0259837 | A1 * | 9/2014 | Belliveau | A61M 5/1415 40/673 |
| 2014/0321096 | A1 * | 10/2014 | Kajackas | A61G 12/00 361/807 |
| 2015/0190567 | A1 * | 7/2015 | Asama | A61M 5/1417 211/85.13 |
| 2015/0196192 | A1 * | 7/2015 | Kan | H04N 5/655 211/85.13 |
| 2015/0224252 | A1 * | 8/2015 | Borges | A61M 5/142 700/282 |

FOREIGN PATENT DOCUMENTS

| | | |
|---|---|---|
| JP | 2004-305280 A | 11/2004 |
| JP | 2010-200775 A | 9/2010 |
| WO | WO-93/02597 A1 | 2/1993 |
| WO | WO-97/01363 A1 | 1/1997 |
| WO | WO-01/36027 A1 | 5/2001 |

OTHER PUBLICATIONS

Extended European Search Report issued in European Patent Application No. 13781587.4 dated Dec. 3, 2015.

* cited by examiner

FIG. 8A
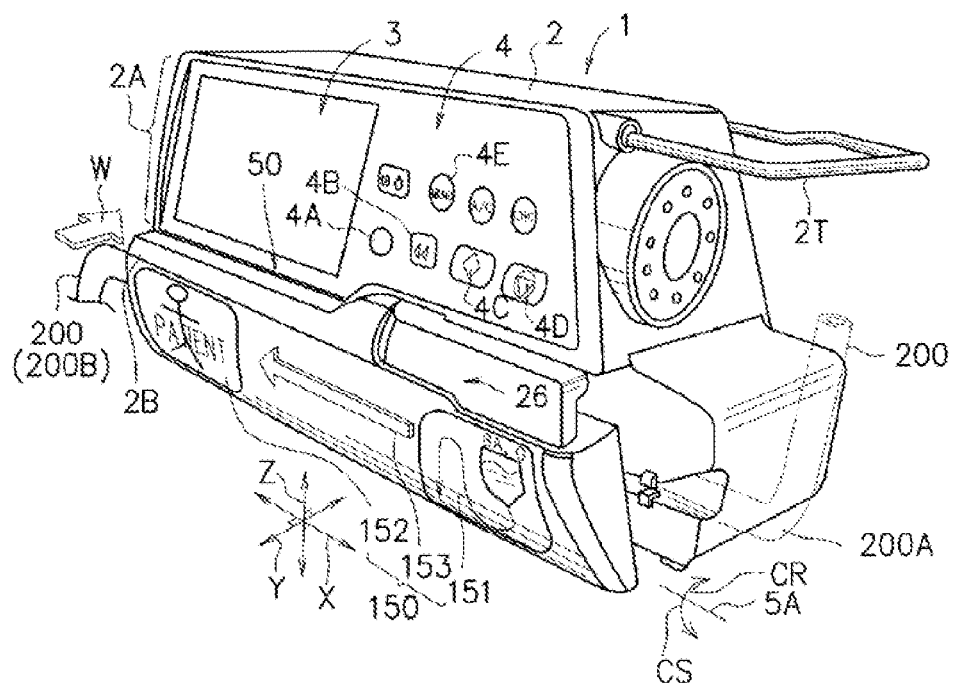
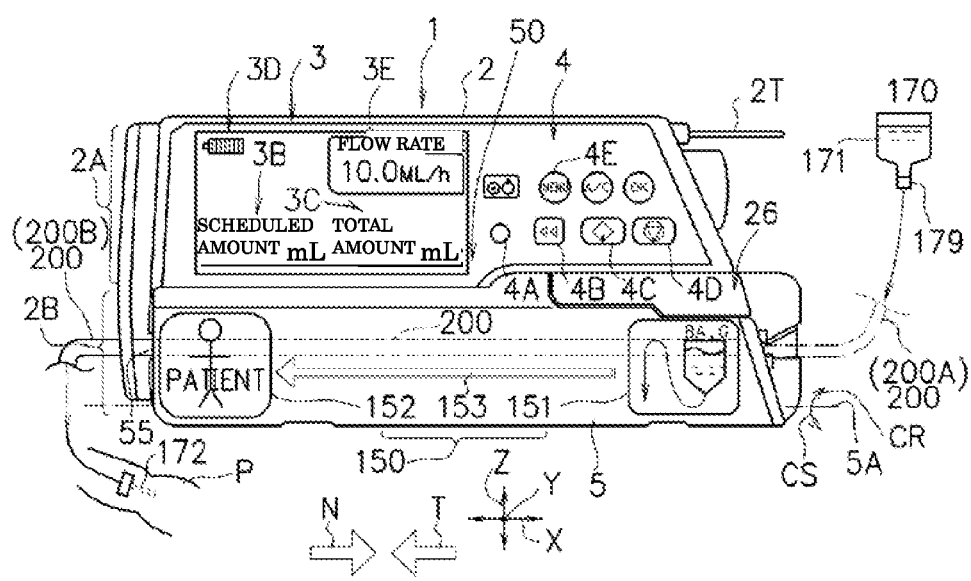
FIG. 8B

FIG. 10A
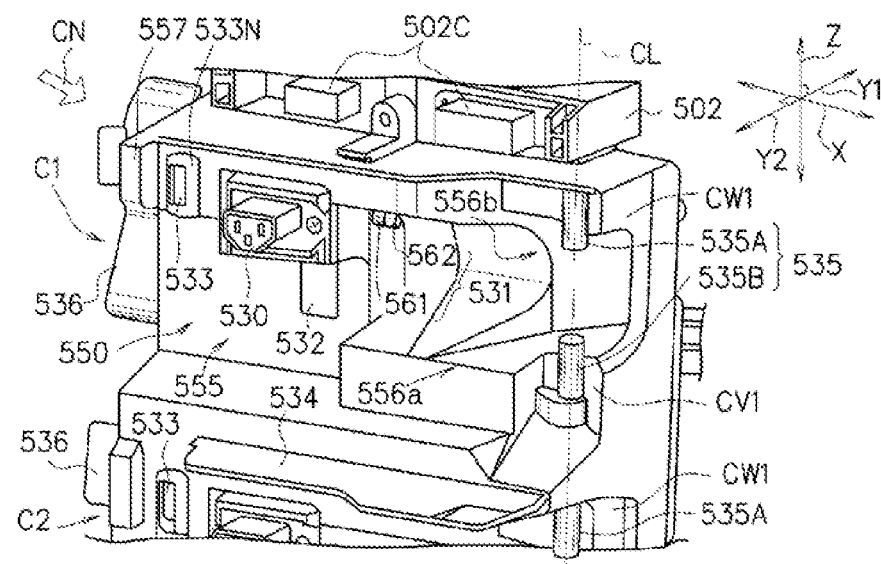
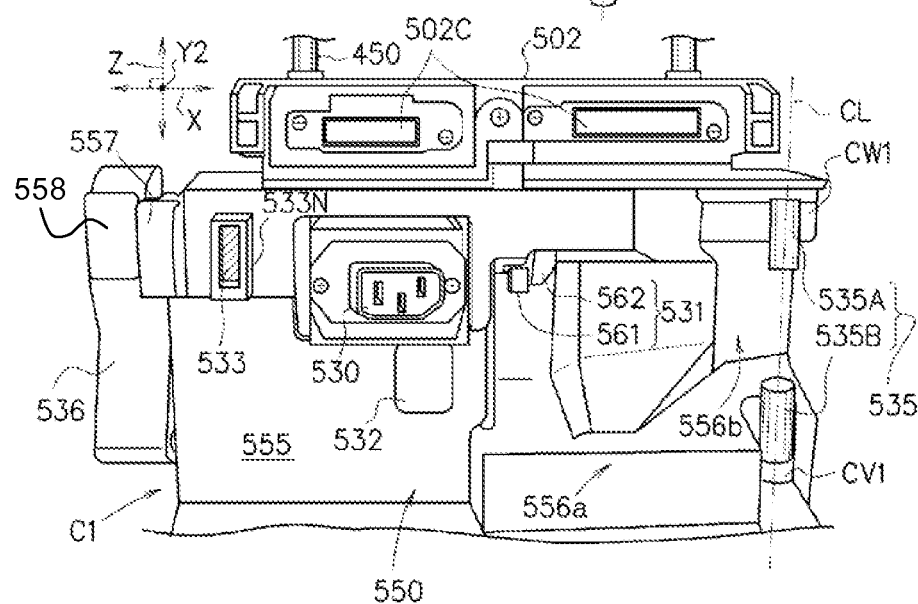
FIG. 10B

FIG. 14A
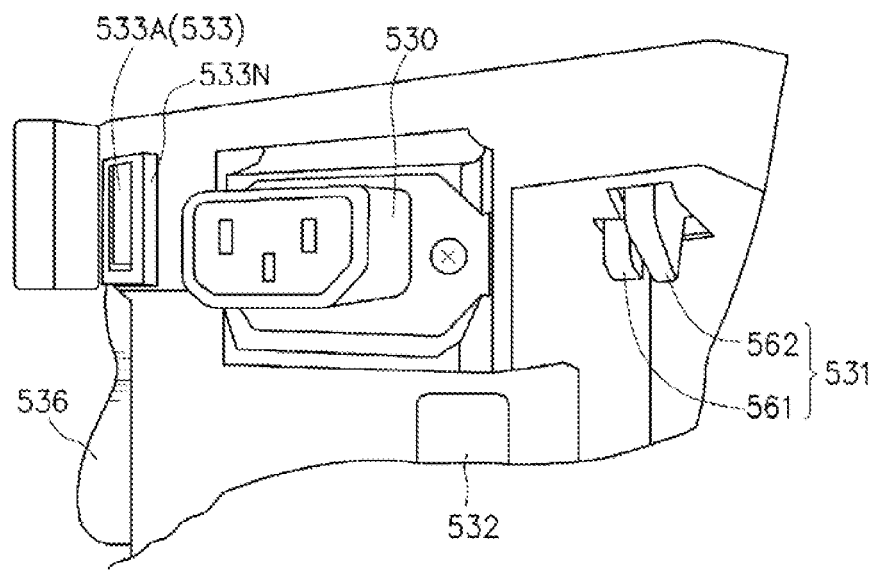
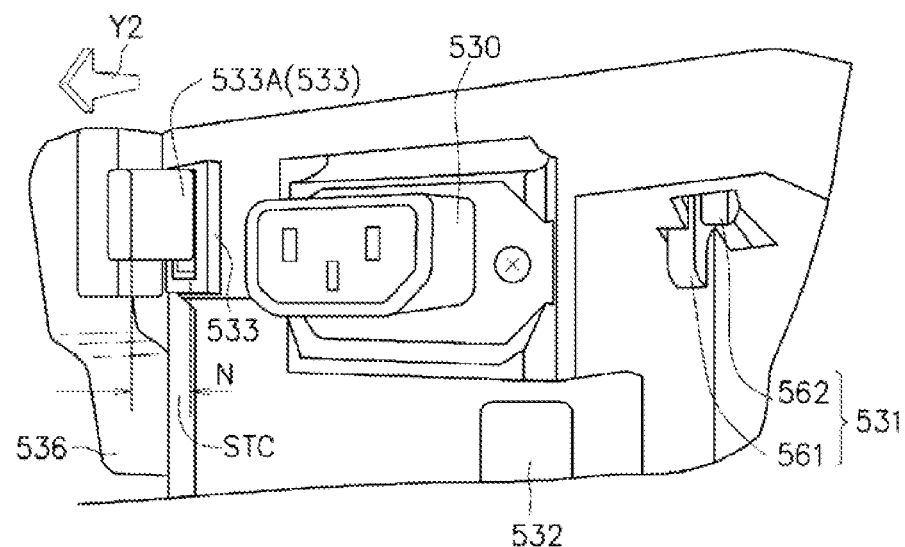
FIG. 14B

FIG. 17A
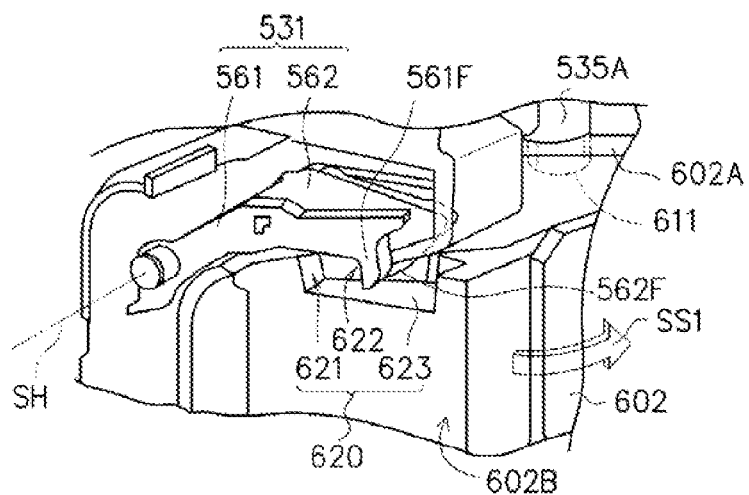
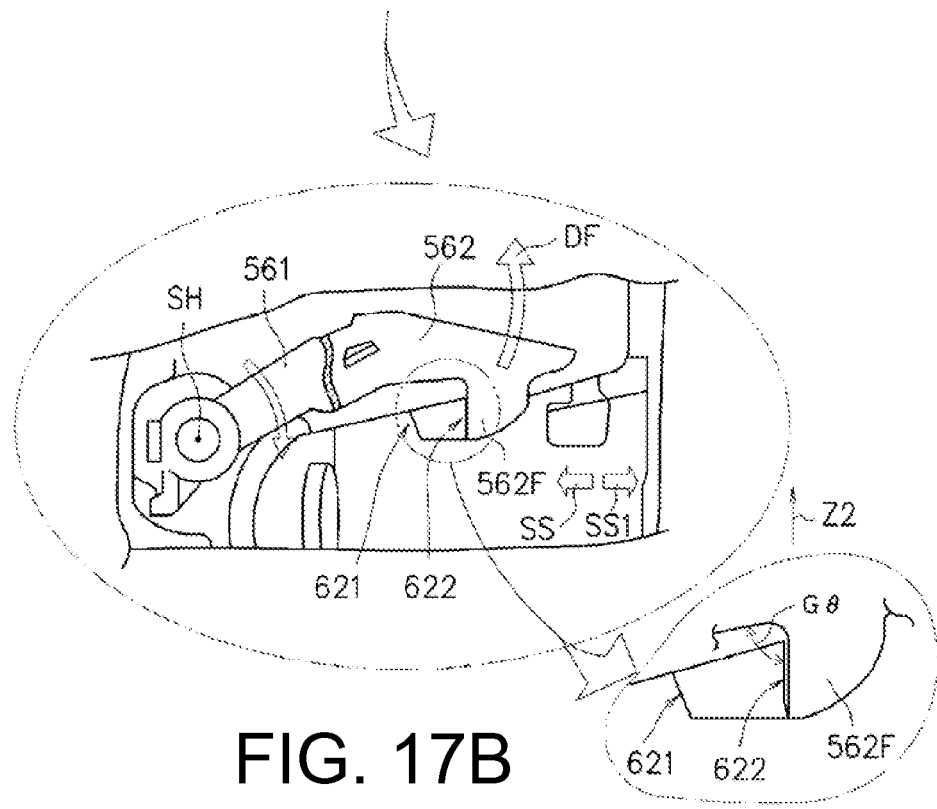
FIG. 17B

FIG. 18A
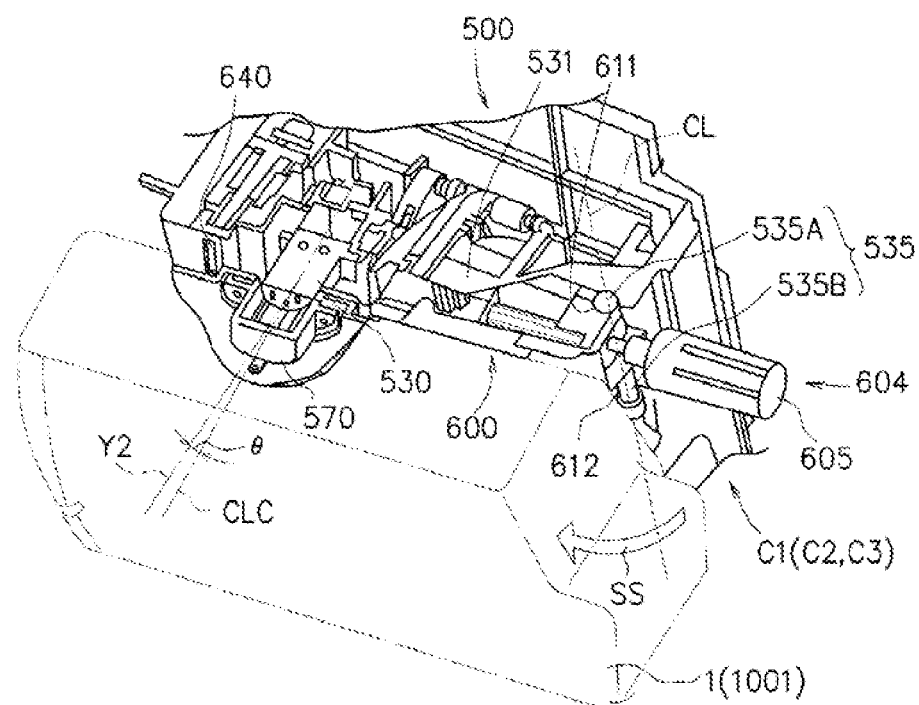
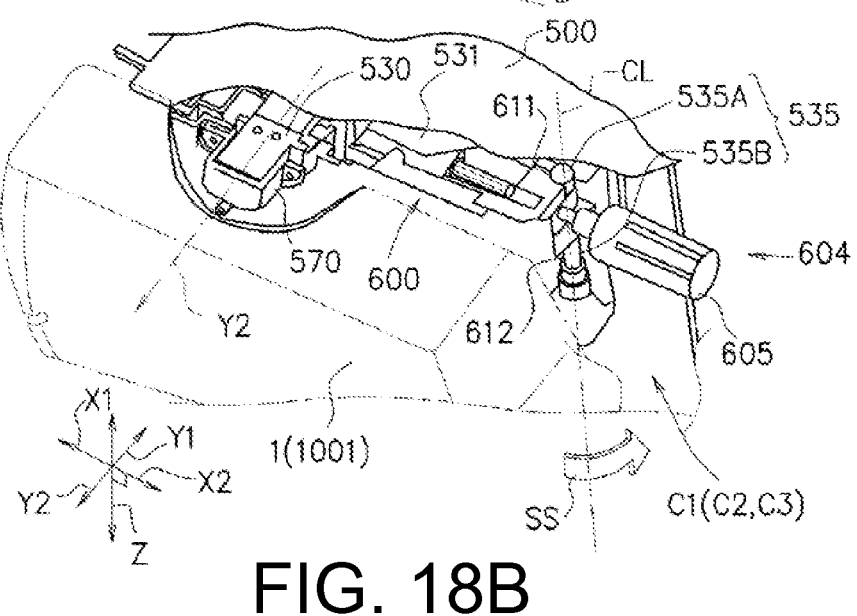
FIG. 18B

FIG. 21A
COMPARATIVE EXAMPLE
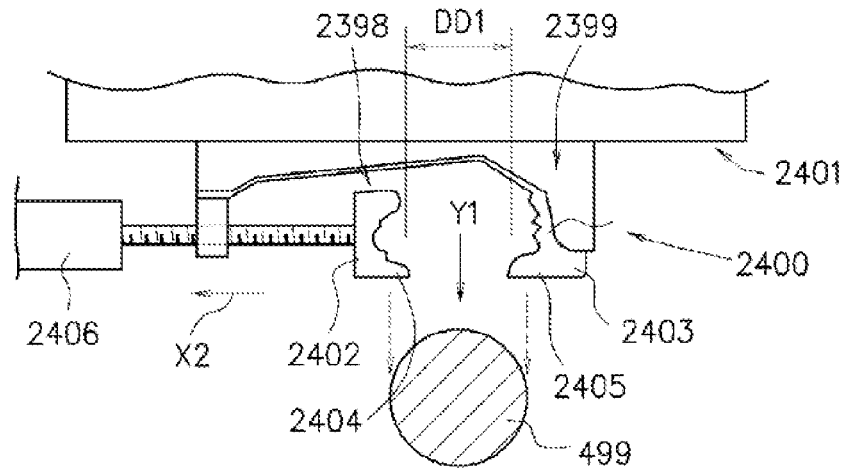
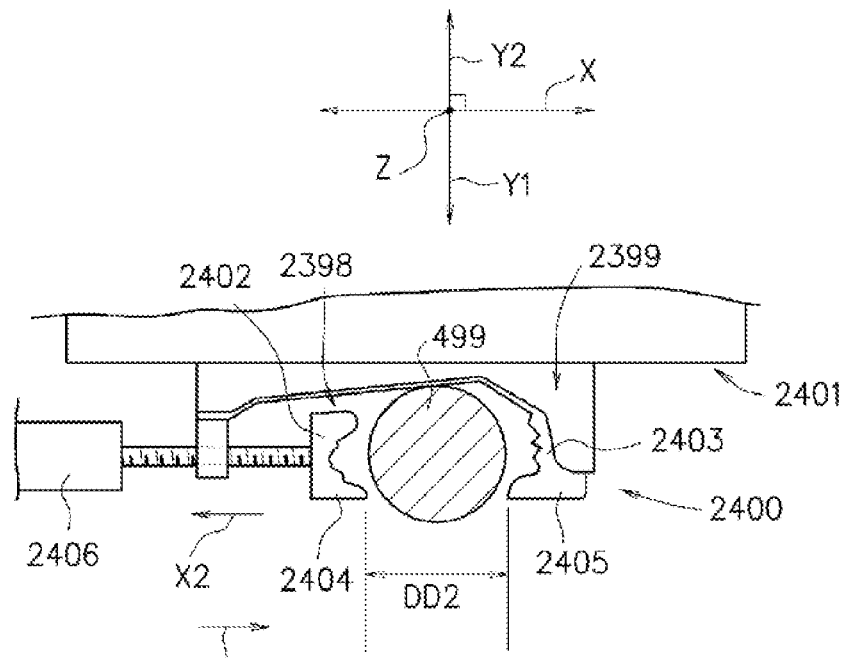
FIG. 21B

FIG. 23A
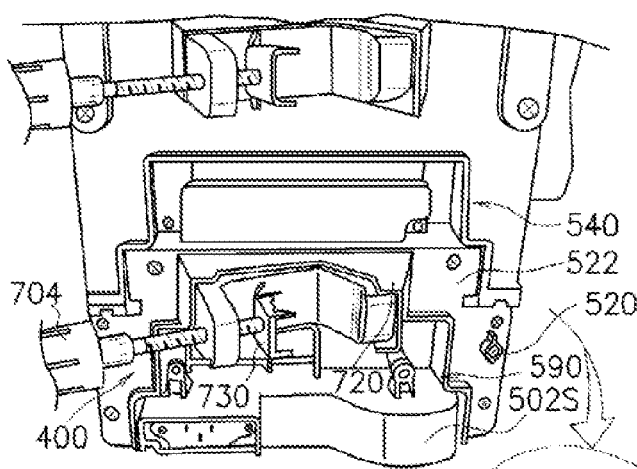
FIG. 23B
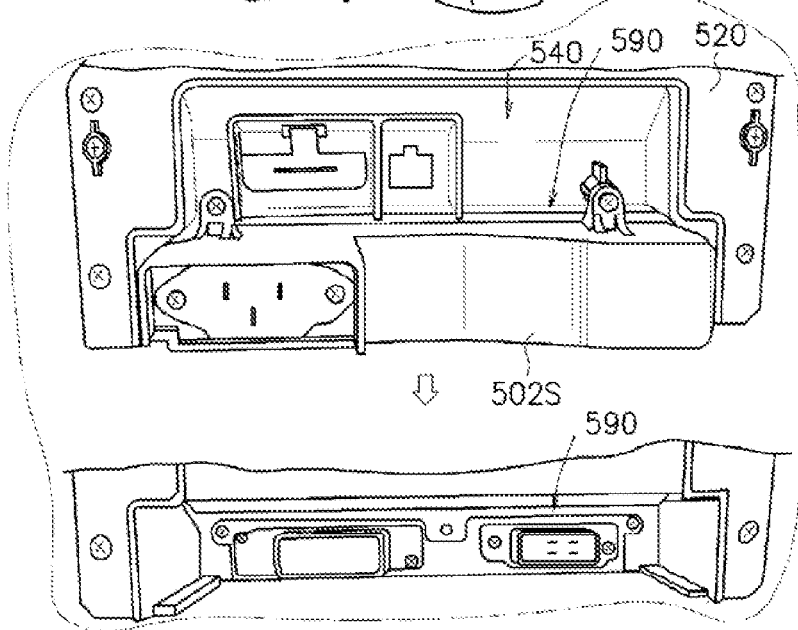
FIG. 23C

MEDICAL APPARATUS RACK

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/061654 filed on Apr. 19, 2013, which is based upon and claims the benefit of priority of Japanese Application No. 2012-098033 filed on Apr. 23, 2012, the entire contents of which are hereby incorporated by reference in their entireties.

BACKGROUND

Technical Field

The present disclosure relates to a medical device rack for holding a medical device such as a syringe pump and an infusion pump to feed a medicine or the like to a patient.

Background Art

An infusion pump and a syringe pump are examples of medical devices used in an intensive care unit (ICU) and the like, for example, and are utilized to feed a medicine to a patient for a relatively long time with high accuracy. An infusion pump is disclosed in JP 2010-200775 A.

According to the infusion pump recited in JP 2010-200775 A, an infusion tube is held by being passed through a main body of the infusion pump in a vertical direction. In contrast, there is a proposed infusion pump in which the infusion tube is held by being passed though the main body of the infusion pump in a horizontal direction. Further, as for the syringe pump, it is proposed that a syringe main body filled with a medicine is horizontally set in the syringe pump, and the syringe pump presses a syringe pusher to accurately feed the medicine inside the syringe main body to a patient side.

Thus, the case of adopting the configuration in which the infusion tube and the syringe are held by being passed in the horizontal direction instead of the vertical direction brings a merit that a plurality of infusion pumps and syringe pumps can be held by being vertically stacked in a rack.

The infusion pump and the syringe pump are medical devices having weight of approximately 1.5 kg to 2.5 kg.

When such devices are lifted and mounted on the rack by a medical staff with both hands, the infusion pump and the syringe pump are mounted by entirely being slid and pushed in the vertical direction to the rack from a front side.

Therefore, sometimes the rack itself may be pushed and moved backward by the infusion pump and the syringe pump. Accordingly, it is difficult for the medical staff to surely mount the relatively heavy infusion pump or syringe pump to the rack while holding the infusion pump or syringe pump with both hands. Also, it is difficult for the medical staff to detach the infusion pump or syringe pump while holding the infusion pump or syringe pump with both hands because the medical staff need to hold the relatively heavy infusion pump or syringe pump with both hands in the same manner as when mounting.

SUMMARY OF INVENTION

Considering the above situation, one objective of certain embodiments of the present invention is to provide a medical device rack in which the medical device can be easily and surely mounted and detached.

According to one embodiment, a medical device rack includes a main body and a mounting section provided at the main body to detachably mount the medical device used in a posture oriented in a lateral direction, wherein the mounting section includes a supporting portion configured to be fitted to the medical device side to support the medical device in a rotatable manner.

According to the above configuration, the supporting portion of the mounting section can support the medical device in a rotatable manner, and therefore, in the case of mounting the medical device to the mounting section or in the case of detaching the medical device from the mounting section, the medical device is partly supported by the supporting portion and can be mounted on the mounting section, or the medical device can be detached from the mounting section in reverse while the medical device is being rotated with one hand. In other words, because the medical device can be mounted on or detached from the rack without necessity of holding the relatively heavy medical device with both hands, the medical device such as an infusion pump and a syringe pump can be easily and surely mounted on or detached from the rack.

In one aspect, a plurality of the mounting sections is provided arranged in a vertical direction of the rack, wherein each of the mounting sections includes an upper wall positioned on an upper portion side of the medical device to be mounted and a lower wall positioned on a lower portion side of the medical device, and the supporting portion includes an upper post projected downward from the upper wall and configured to be detachably fitted into a rear surface portion side of the medical device and a lower post projected upward from the lower wall and configured to be detachably fitted into the rear surface portion side of the medical device.

According to the above configuration, the upper post and lower post of the supporting portion are fitted into the rear surface portion side of the medical device, thereby supporting the medical device in a rotatable manner. Accordingly, despite such a simple configuration, in the case of mounting the medical device to the mounting section or detaching the medical device from the mounting section, the medical device is partly supported by the supporting portion and the medical device can be mounted on the mounting section or the medical device can be detached from the mounting section in reverse while the medical device is rotated with one hand.

In one aspect, the mounting section includes a lock mechanism configured to detachably fix the medical device to the mounting section by being engaged with the rear surface portion side of the medical device.

According to the above configuration, the lock mechanism is engaged with the rear surface portion side of the medical device positioned at the mounting section, and therefore, the medical device can be surely and mechanically locked and fixed to the mounting section.

In one aspect, a supporting projected portion configured to support a lower portion of the medical device is provided on the lower wall.

According to the above configuration, the supporting projected portion can support the lower portion of the medical device in the case where the medical device is rotated around the supporting portion to be mounted on the mounting section or the medical device is rotated around the supporting portion to be detached from the mounting section. Therefore, the relatively heavy medical device can be safely mounted and detached.

In one aspect, the mounting section is provided with an outlet terminal configured to electrically connect the medical device with the rack by being inserted into an outlet receiving portion provided at the medical device when the medical device is mounted on the mounting section, and the outlet terminal is disposed at the mounting section along a rotary direction of the outlet receiving portion of the medical device around the supporting portion.

According to the above configuration, the outlet terminal is disposed at the mounting section along the rotary direction of the outlet receiving portion of the medical device around the supporting portion. Therefore, the outlet terminal on the mounting section side can be surely connected to the outlet receiving portion on the medical device side when the medical device is rotated around the supporting portion to be mounted on the mounting section.

In one aspect, the outlet terminal includes an energizing member disposed in the rotary direction around the supporting portion in the mounting section, and when the medical device is mounted on the mounting section, the outlet terminal is fitted into the outlet receiving portion by being pushed in the rotary direction around the supporting portion against force of the energizing member.

According to the above configuration, the outlet terminal on the mounting section side can be surely connected to the outlet receiving portion on the medical device side by utilizing force of a spring when the medical device is rotated around the supporting portion to be mounted on the mounting section. Further, when the medical device is rotated around the supporting portion to be detached from the mounting section, the outlet terminal on the mounting section side can be returned again in the rotary direction around the supporting portion by utilizing the force of the spring.

In one aspect, the supporting portion is detachably fitted to a pole clamp configured to mount the medical device to a pole.

According to the above configuration, the supporting portion on the mounting section side can detachably support the medical device by utilizing the pole clamp on the medical device side.

In one aspect, the medical device is an infusion pump that includes a main body case, a display unit configured to display information, an operation panel including an operation button, a tube mounting section where an infusion tube for feeding a medicine is mounted, and an access cover configured to cover the tube mounting section. The display unit and operation panel are disposed at an upper portion of the main body case, and the tube mounting section and the access cover are disposed at a lower portion of the main body case.

According to the above configuration, the infusion pump can be detachably mounted on the mounting section of the rack.

In one aspect, the medical device is a syringe pump that includes a main body case, a display unit configured to display information, an operation panel including an operation button and a syringe mounting section where a syringe for feeding a medicine is mounted. The display unit and operation panel are disposed at an upper portion of the main body case, and the syringe mounting section is disposed at a lower portion of the main body case.

According to the above configuration, the syringe pump can be detachably mounted on the mounting section of the rack.

Certain embodiments of the present invention can provide a medical device rack in which the medical device can be easily and surely mounted and detached.

BRIEF DESCRIPTION OF DRAWINGS

FIG. 8A is a front side perspective view illustrating an exemplary configuration of an infusion pump.

FIG. 8B is a front view illustrating the infusion pump of FIG. 8A.

FIG. 10A is a perspective view illustrating a first mounting section out of the first mounting section, a second mounting section, and a third mounting section illustrated in FIG. 2.

FIG. 10B is a perspective view of the first mounting section illustrated in FIG. 10A viewed from the front side.

FIG. 14A is a diagram illustrating a state in which the pusher is housed inside a housing portion.

FIG. 14B is a diagram illustrating a state in which the pusher is projected from the housing portion by an amount of a predetermined stroke STC.

FIG. 17A is a view illustrating a state in which the infusion pump is properly fixed by engaging the second claw portion of the lock mechanism illustrated in FIGS. 14A and 14B with the second stepped portion of the engagement portion at a second projected portion.

FIG. 17B is a side perspective view illustrating a state in which the infusion pump is properly fixed by engaging the second claw portion of the lock mechanism illustrated in FIGS. 14A and 14B with the second stepped portion of the engagement portion at the second projected portion.

FIG. 18A is a view illustrating a state in which the infusion pump is mounted on the first mounting section of the rack by rotating the infusion pump around a supporting portion in an SS-direction as an example.

FIG. 18B is a view illustrating a state in which the infusion pump is mounted on the first mounting section of the rack by rotating the infusion pump around the supporting portion rotated slightly more than shown in FIG. 18A.

FIG. 21A is a diagram illustrating a mounting configuration of a pole clamp generally applied as a comparative example of the pole clamp according to the embodiment of the present invention showing the pole away from the clamp.

FIG. 21B is a diagram illustrating a mounting configuration of the pole clamp generally applied as a comparative example of the pole clamp according to the embodiment of the present invention showing the pole next to the clamp.

FIG. 23A is a rear perspective view illustrating the lower portion of the rack and the rear surface portion side of the communication box mounted on the lower portion.

FIG. 23B is a rear perspective view illustrating the rear surface portion side of the communication box.

FIG. 23C is a rear perspective view illustrating the rear surface portion side of the communication box shown without an inlet box for additional AC power supply.

DETAILED DESCRIPTION

A preferred embodiment of the present invention will be described below in detail with reference to the drawings.

Because the embodiment described below is an example of the present invention, various technical limitations are stated; however, note that the scope of the present invention is not limited thereto unless otherwise particularly specified in the following description to limit the present invention.

Figure 1:
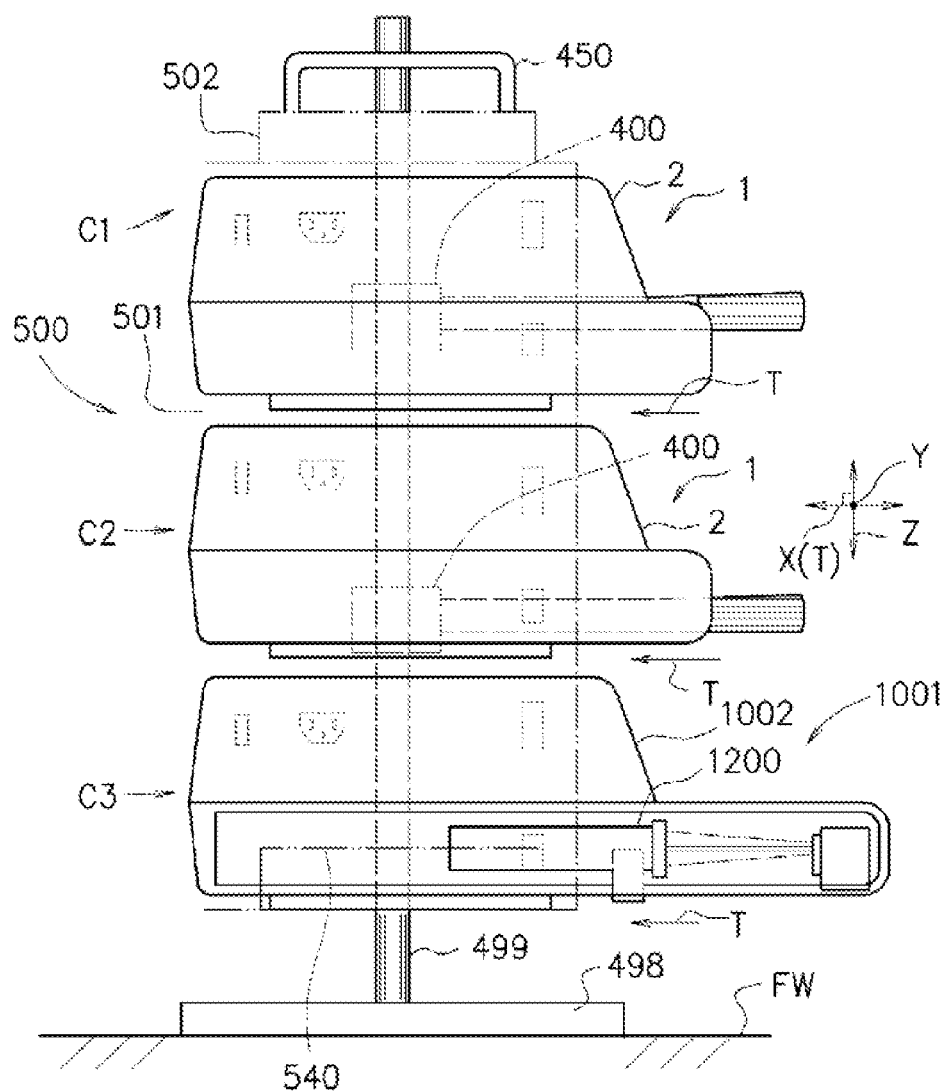
FIG. 1 is a front view illustrating an embodiment of a medical device rack according to the present invention.
Figure 2:
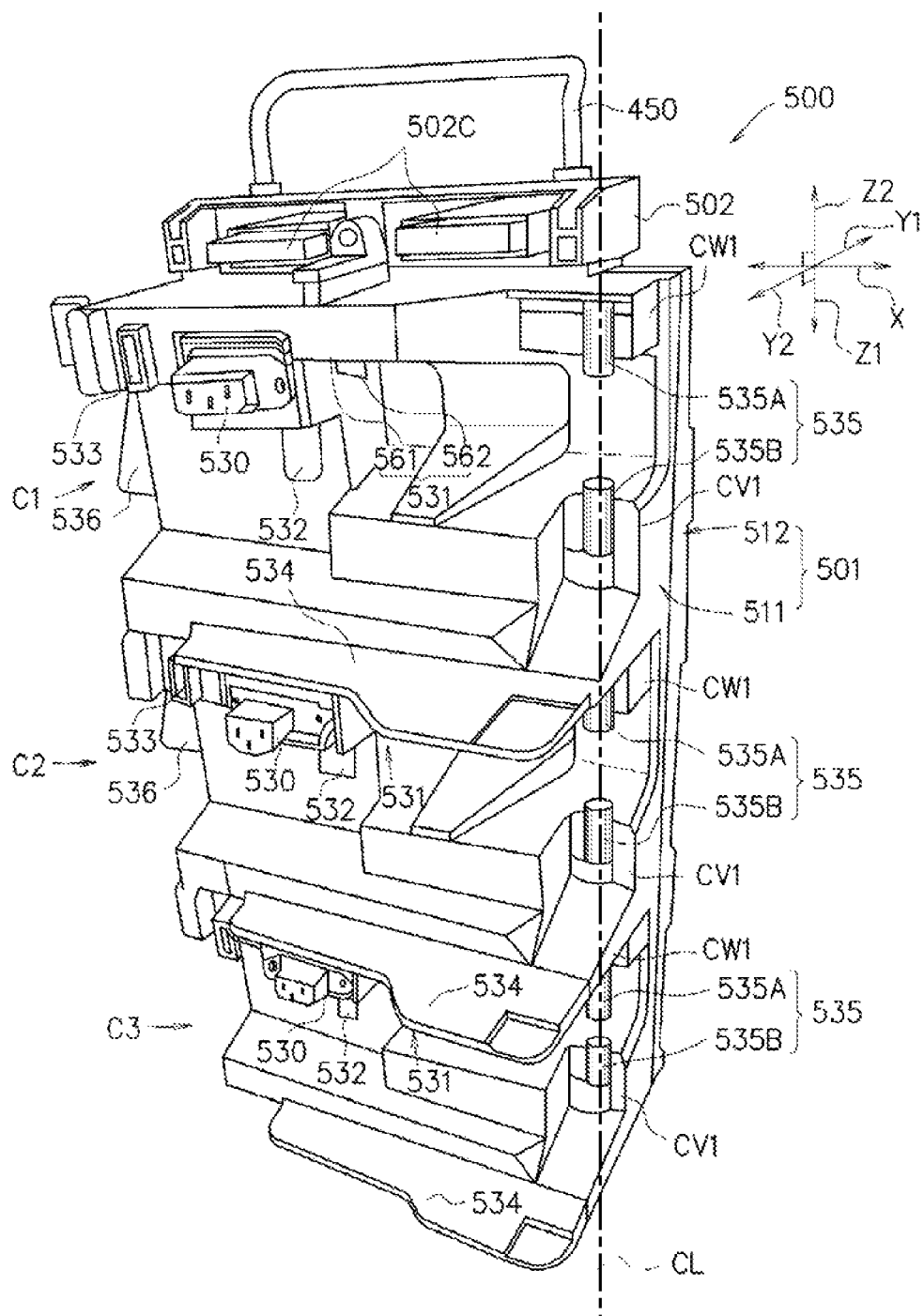
FIG. 2 is a perspective view of a front side of the rack illustrated in FIG. 1, obliquely viewed from an upper right side.
Figure 3:
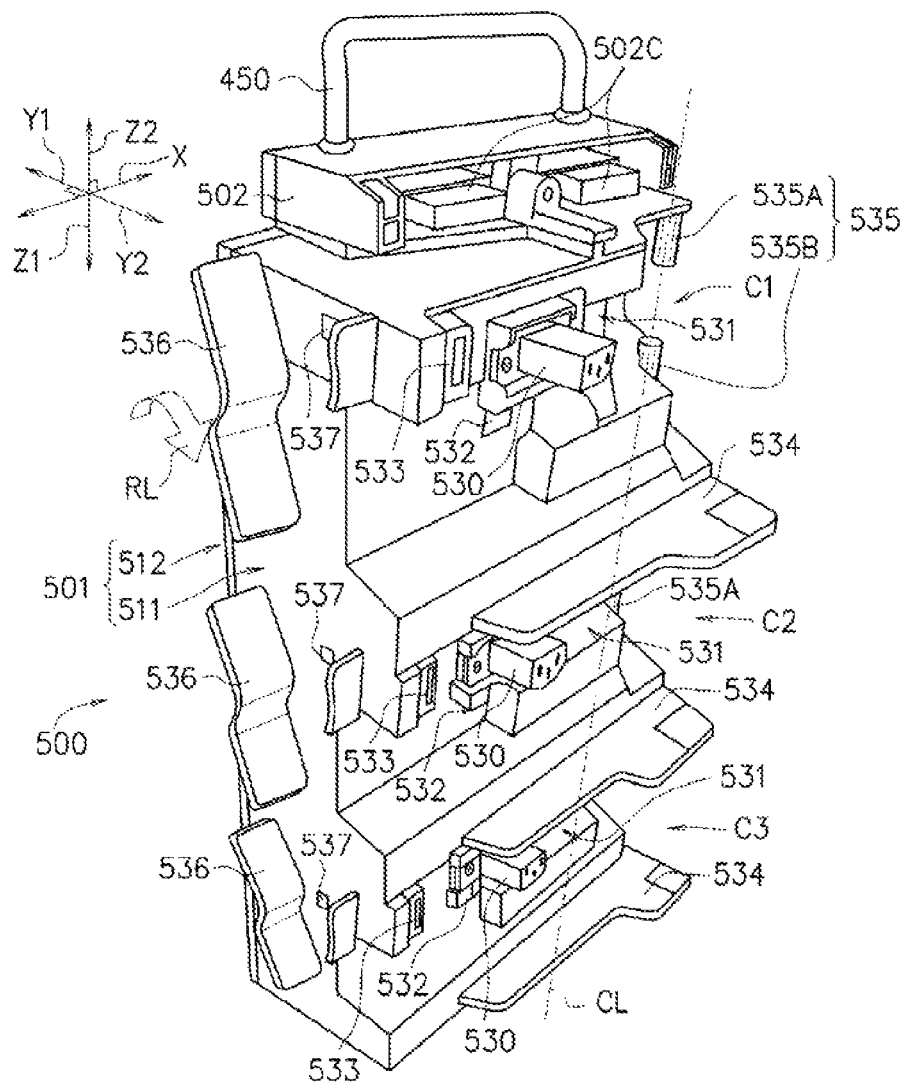
FIG. 3 is a perspective view of the front side of the rack illustrated in FIG. 1, obliquely viewed from an upper left side.

FIG. 1 is a front view illustrating an embodiment of a medical device rack according to the present invention. FIG. 2 is a perspective view of a front side of the rack illustrated in FIG. 1, obliquely viewed from an upper right side. FIG. 3 is a perspective view of the front side of the rack illustrated in FIG. 1, obliquely viewed from an upper left side.

As illustrated in FIG. 1, a rack 500 can be detachably mounted to a pole 499 standing upright. The pole 499 is set standing vertical (Z-direction) to a base body 498, and the base body 498 is disposed on a floor surface FW of a medical ward, a treatment room, or the like. As illustrated in FIG. 1, one rack 500 is mounted to the pole 499, but a plurality of the racks 500, for example three racks 500, can be also mounted in a stacking manner in the Z-direction by selecting a longer pole 499.

In FIG. 1, X-direction, Y-direction, and Z-direction are orthogonal to each another, and the Z-direction is a vertical direction. The X-direction is a horizontal direction and corresponds to a right-left direction of the rack 500, an infusion pump 1, or a syringe pump 1001. The X-direction is also a medicine feeding direction (T-direction) in the infusion pump 1 or syringe pump 1001. The Y-direction is a front-rear direction of the rack 500, infusion pump 1, or syringe pump 1001.

In the rack 500 illustrated in FIG. 1, for example, three medical devices are mounted, and in the example of FIG. 1, two infusion pumps 1 and one syringe pump 1001 are detachably mounted in a stacking manner sequentially from the top. Note that an outer shape of a main body case 2 of the infusion pump 1 and an outer shape of a main body case 1002 of the syringe pump 1001 are common while exemplary configurations of the infusion pump 1 and the syringe pump 1001 will be described later.

The rack 500 illustrated in FIG. 1 includes a main body 501, an upper connecting portion 502, and a connection-receiving portion 540 as a lower connecting portion, a handle 450, and a plurality of pole clamps 400 for the rack 500. The main body 501 of the rack 500 is detachably fixed to the pole 499 by using the plurality of pole clamps 400 for the rack.

As illustrated in FIGS. 2 and 3, the main body 501 of the rack 500, the upper connecting portion 502, and the lower connection-receiving portion 540 (see FIG. 1) are preferably integrally formed of molding resin material having chemical resistance, and include a splash proof structure whereby the medicine or the like can be prevented from entering inside even when a medicine or the like is splashed and adhered. The main body 501 of the rack 500 is formed by combining a front case 511 with a rear case 512. The upper connecting portion 502 is used when a different rack 500 having the same structure is additionally stacked and connected above the upper portion of the rack 500. Or, the upper connecting portion 502 is used when the communication box later described is detachably mounted. The lower connection-receiving portion 540 is used when a different rack 500 having the same structure is additionally connected at the lower portion of the rack 500 by inserting the upper connecting portion 502 of the rack 500. The lower connection-receiving portion 540 may also be used when the communication box is detachably mounted. The metal-made handle 450 having a U-shape is gripped by a medical staff at the time of carrying the rack 500. The handle 450 is fixed to an upper surface of the upper connecting portion 502.

The main body 501 of the rack 500 illustrated in FIGS. 1 to 3 includes a first mounting section C1, a second mounting section C2, and a third mounting section C3 sequentially from the top. The infusion pump 1, infusion pump 1, and syringe pump 1001 are detachably mounted on the first mounting section C1, second mounting section C2, and third mounting section C3 respectively according to a mounting example illustrated in FIG. 1. Because the first mounting section C1, second mounting section C2, and third mounting section C3 have the same structure, any of the infusion pump 1 and syringe pump 1001 can be detachably mounted on any of the mounting sections.

In the rack 500 illustrated in FIGS. 2 and 3, the upper connecting portion 502 of the main body 501 and the handle 450 are exposed. However, in the rack 500 illustrated in FIGS. 4A to 7, the communication box 520 is detachably mounted on the upper connecting portion 502 of the main body 501.

Figures 4A, 4B:
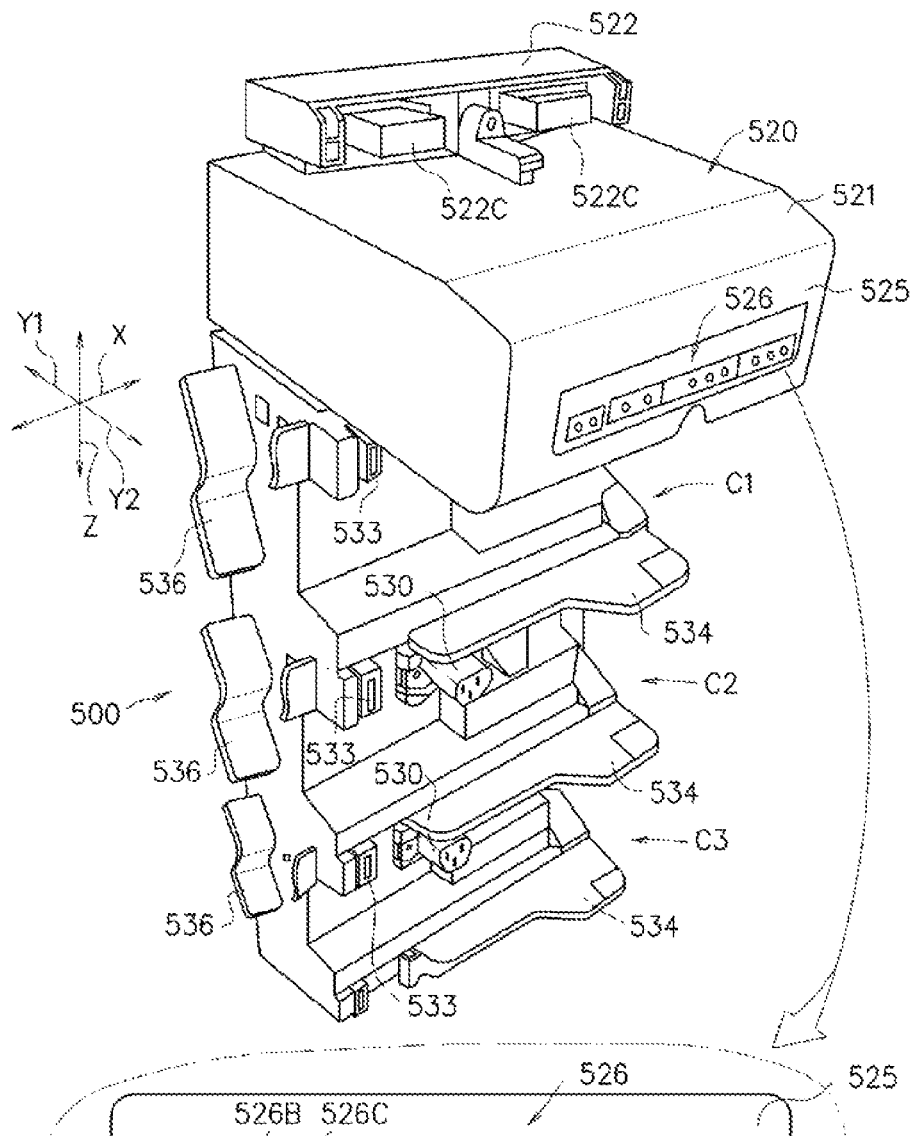
FIG. 4A is a perspective view illustrating a front side of a main body of the rack and a communication box mounted on the main body, obliquely viewed from the left side.
FIG. 4B is a front view of a portion of the communication box shown in FIG. 4A.
Figure 5:
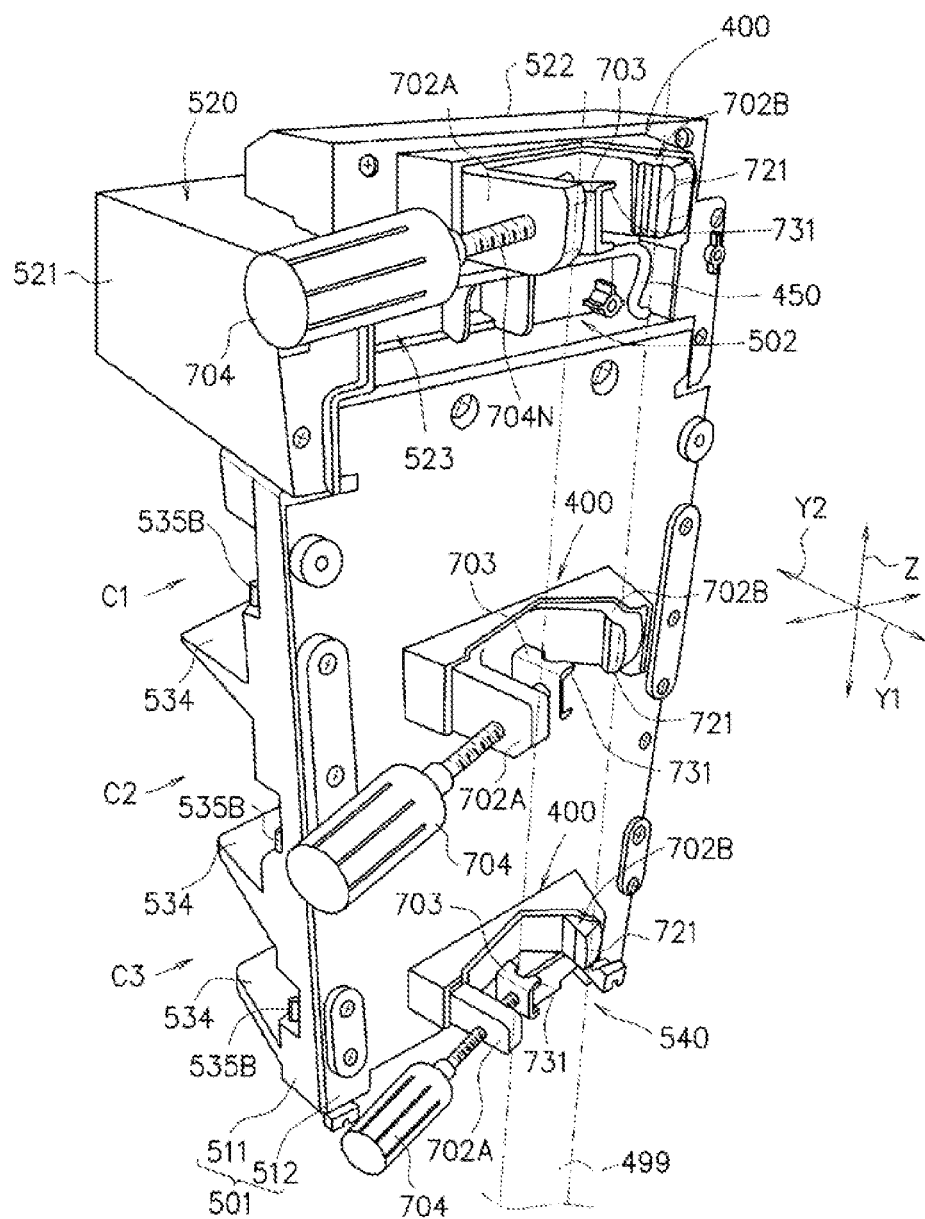
FIG. 5 is a perspective view illustrating a rear side of the main body of the rack and the communication box, obliquely viewed from the left side.
Figure 6:
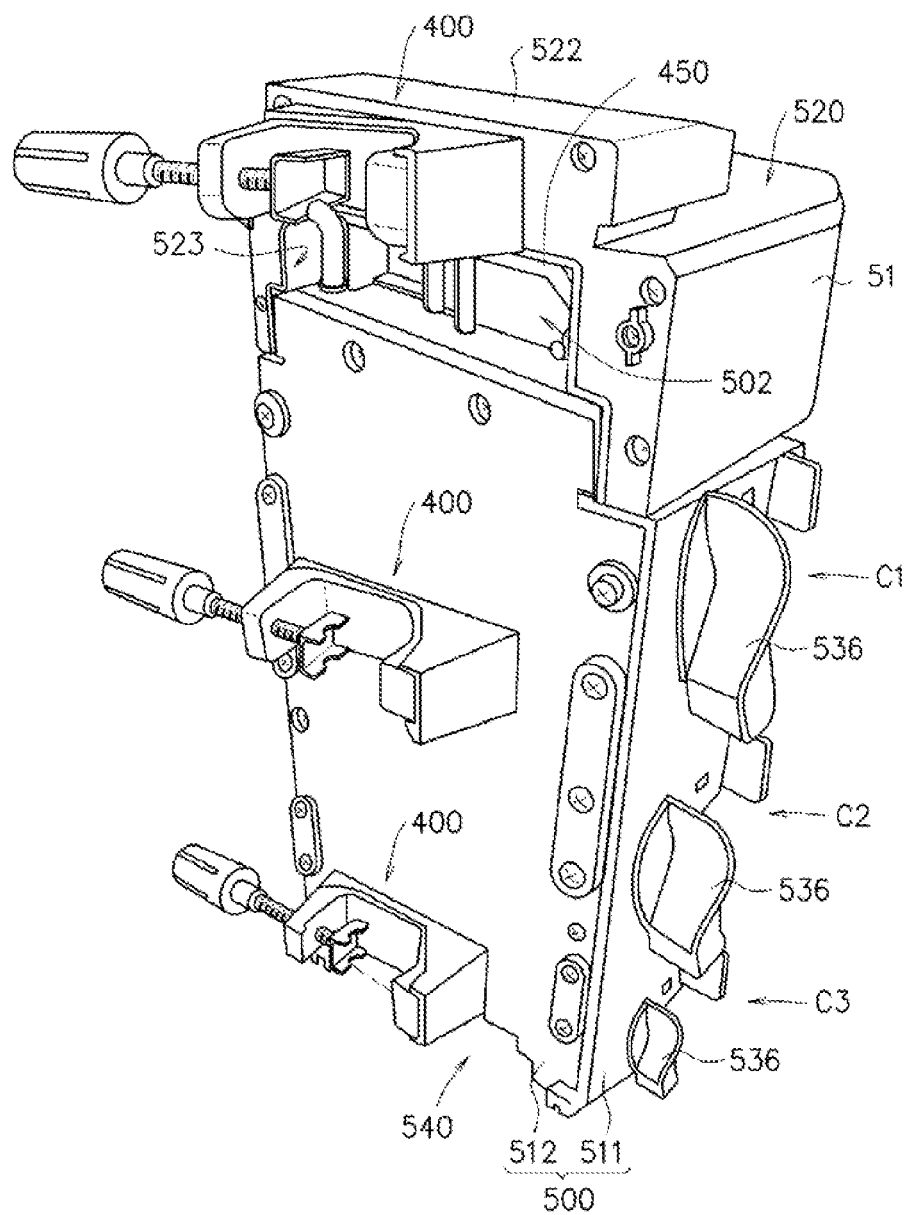
FIG. 6 is a perspective view illustrating the rear side of the main body of the rack and the communication box, obliquely viewed from the right side.
Figure 7:
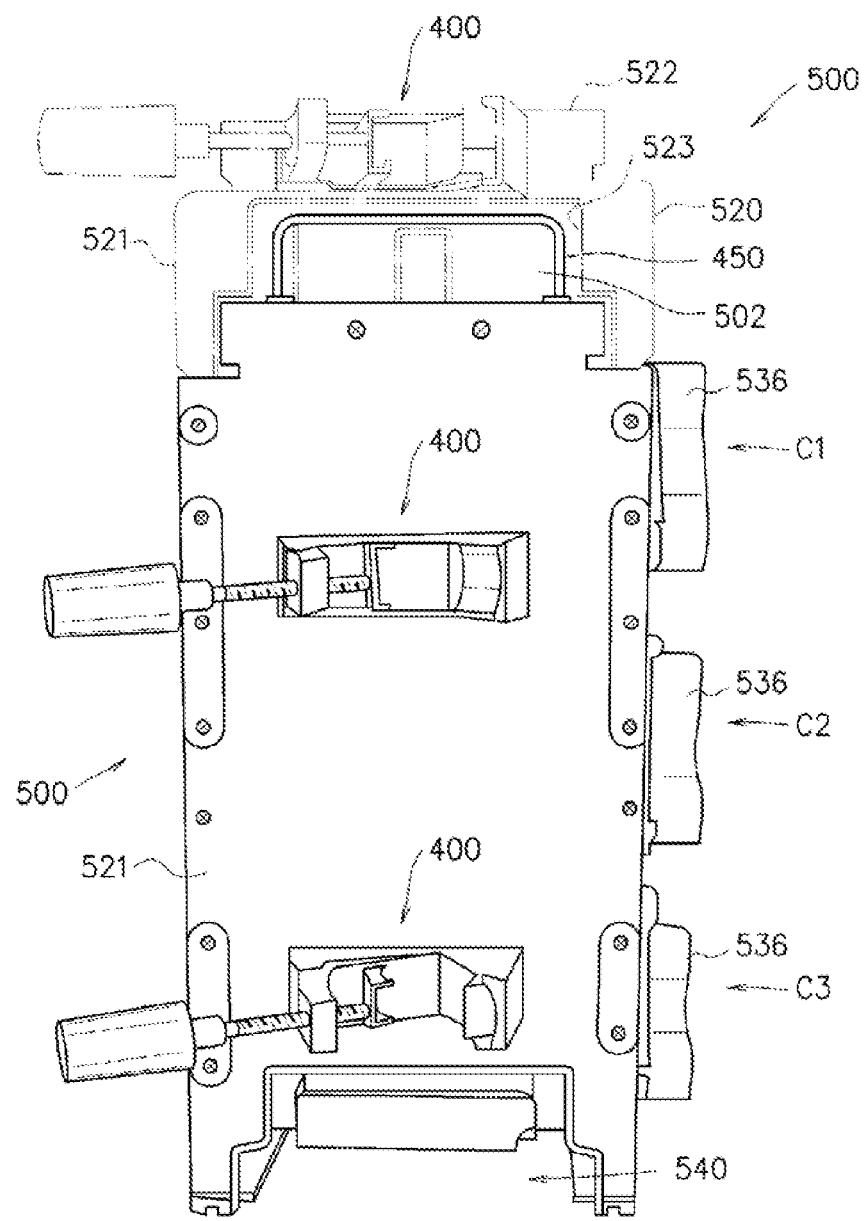
FIG. 7 is a perspective view illustrating the rear side of the main body of the rack and the communication box.

FIG. 4A is a perspective view illustrating a front side of a main body 501 of the rack 500 and a communication box 520 mounted on the main body 501, obliquely viewed from the left side. FIG. 4B is a front view of a portion of the communication box 520 shown in FIG. 4A. FIG. 5 is a perspective view illustrating a rear side of the main body 501 of the rack 500 and the communication box 520, obliquely viewed from the left side. FIG. 6 is a perspective view illustrating a rear side of the main body 501 of the rack 500 and the communication box 520, obliquely viewed from the right side, and FIG. 7 is a view illustrating the rear side of the main body 501 of the rack 500 and the communication box 520.

As illustrated in FIGS. 4A to 7, the communication box 520 is additionally mounted on the rack 500 in order to exchange necessary information with an external device such as an external computer by optical communication using, for example, infrared or the like. As illustrated in FIGS. 4A and 5, the communication box 520 includes a housing 521, a connecting portion 522, a pole clamp 400, and a connection-receiving portion 523 having a recessed shape. The housing 521 illustrated in FIG. 4A has a box shape, and the connecting portion 522 is disposed on an upper portion of the housing 521. The connecting portion 522 has a shape in common with the above-described connecting portion 502 of the main body 501 illustrated in FIG. 3 as having a same size and a same configuration as the connecting portion 502.

The pole clamp 400 of the communication box 520 illustrated in FIG. 5 is disposed on a rear surface of the connecting portion 522, and the pole clamp 400 of the communication box 520 is same as the two pole clamps 400 on the main body 501 side. A distance in the Z-direction between the pole clamp 400 of the communication box 520 and the pole clamp 400 on the upper side of the main body 501 is set same as a distance between the two pole clamps 400 of the main body 501. With this configuration, the main body 501 and the communication box 520 are stably fixed to the pole 499 at an equal interval by using the three pole clamps 400.

Particularly, the communication box 520 is also provided with the pole clamp 400 because the communication box 520 is heavy. Therefore, there is merit in the pole 499 surely and stably fixing the rack 500 and the communication box 520 mounted on at least one of the upper portion of the rack 500 and the lower portion of the rack 500. When the communication box 520 is mounted on at least one of the upper portion of the rack 500 and the lower portion of the rack 500, the communication box 520 is electrically connected among two infusion pumps 1 and one syringe pump 1001 mounted on the first mounting section C1 to the third mounting section C3 via the rack 500. Therefore, the two infusion pumps 1 and one syringe pump 1001 can exchange the necessary information with the external computer via the communication box 520. Note that a configuration of the pole clamp 400 will be described later.

As illustrated in FIGS. 5 and 6, the communication box 520 is slid in Y1-direction (rear side in the front-rear direction) with respect to the connecting portion 502 and the upper connecting portion 502 and the handle 450 of the rack 500 are inserted into the connection-receiving portion 523 of the communication box 520. Due to this, the communication box 520 is mechanically and electrically connected to the main body 501 of the rack 500 by using the upper connecting portion 502 and handle 450. Thus, the communication box 520 illustrated in FIG. 5 can be mounted on a more upper portion of the first mounting section C1 of the main body 501 of the rack 500 by the above-described insertion in the Y1-direction. Further, the communication box 520 can be slid in Y2-direction (front side in the front-rear direction) with respect to the connecting portion 502 in reverse, thereby detaching the communication box 520 from the upper connecting portion 502 and the handle 450 of the rack 500.

The connecting portion 522 of the communication box 520 includes a connector 522C for communication as illustrated in FIG. 4A. As illustrated in FIGS. 4A and 4B, a display unit 526 is provided on a front surface 525 of the housing 521 of the communication box 520. The display unit 526 includes, for example, a power switch 526A, a power plug inserted lamp 526B, a lamp 526C indicating a commercial AC power source or battery power source, a group of lamps 526D indicating communication levels, and so on.

Now, configurations of the first mounting section C1, second mounting section C2, and third mounting section C3 of the main body 501 of the rack 500 will be described with reference to FIGS. 2 and 3.

The configurations of the first mounting section C1, second mounting section C2, and third mounting section C3 illustrated in FIGS. 2 and 3 are substantially the same. Therefore, the first mounting section C1 will be representatively described below, and components common in the first mounting section C1, second mounting section C2, and third mounting section C3 will be denoted by the same reference signs.

As illustrated in FIGS. 2 and 3, the first mounting section C1 includes an outlet terminal 530 for power connection, a lock mechanism 531, an IrDA 532, a pusher 533, a tray 534, a supporting portion 535, an operation lever 536, and an indicator 537.

The supporting portion 535 illustrated in FIG. 2 includes a upper post 535A and a lower post 535B facing each other on a same axis and having an outside diameter, a length, and quality of material which are the same. The upper post 535A is fixed downward in Z1-direction at an upper wall CW1 of the first mounting section C1, and the lower post 535B is fixed upward in Z2-direction at a lower wall CV1 of the first mounting section C1. The upper post 535A and lower post 535B can be detachably mounted on the pole clamp for a pump (later described) of the infusion pump 1 or the syringe pump 1001. A rotary center shaft CL passing through the upper post 535A and lower post 535B is a rotary support center in the case of mounting the infusion pump 1 or the syringe pump 1001 to the first mounting section C1 while executing rotating operation.

As illustrated in FIG. 3, the operation lever 536 is mounted such that a medical staff can manually execute the rotational operation in RL direction (frontward direction) at a left-side surface portion of the front case 511 as illustrated in FIG. 3. The indicator 537 is provided on a front side of the operation lever 536 at the left-side surface portion of the front case 511. While a configuration and a function of the indicator 537 will be described later, the indicator 537 has a function to indicate, for the medical staff, whether the infusion pump 1 or the syringe pump 1001 is surely locked by the lock mechanism 531 illustrated in FIG. 2 and properly fixed to the first mounting section C1, or whether the infusion pump 1 or the syringe pump 1001 is still temporarily fixed to the first mounting section C1 by using a blue color indication and a red color indication, for example. The above described is the configuration of the first mounting section C1, and; note that the second mounting section C2 and the third mounting section C3 have the same configuration.

The upper connecting portion 502 illustrated in FIGS. 2 and 3 includes an inlet box 502C for AC power supply.

As illustrated in FIG. 7, the connection-receiving portion 540 configured to receive the upper connecting portion 502 of the different rack 500 by inserting the upper connecting portion 502 is provided at the lower portion of the main body 501 of the rack 500. The connection-receiving portion 540 has a recessed shape same as the recessed shape of the connection-receiving portion 523 of the communication box 520. The connection-receiving portion 540 is used to electrically and mechanically connect the upper connecting portion 502 of the different rack 500 to lower side of the rack 500. Alternately, the connection-receiving portion 540 is used to electrically and mechanically connect the connecting portion 522 having a projected shape of the different communication box 520 that has the same shape as the communication box 520 illustrated in FIG. 7.

Now, a configuration of the infusion pump 1 exemplified in FIG. 1 will be described with reference to FIGS. 8A and 8B, and a configuration of the syringe pump 1001 will be described with reference to FIG. 9.

First, the exemplary configuration of the infusion pump 1 will be described with reference to FIGS. 8A and 8B. FIG. 8A is an external perspective view illustrating a preferred embodiment of the infusion pump according to the present invention. FIG. 8B is a front view of the infusion pump 1 illustrated in FIG. 8A, viewed from W-direction.

The infusion pump 1 illustrated in FIGS. 8A and 8B can exchange information such as operational information of the infusion pump 1, medicine information, etc. with the external computer via a communication network such as hospital radio or wired LAN by using the rack 500 and the communication box 520. The infusion pump 1 is used in, for example, intensive care unit (ICU, CCU, NICU) or the like, and is an injection pump used for injecting, to a patient, medicines such as anticancer drug, anesthetic, chemotherapeutic agent, and nutrients and blood transfusion or the like for a long time with high accuracy. The infusion pump 1 can feed a selected medicine by selecting and obtaining information of the medicine to be used from a medicine library, for example, by using the rack 500 and the communication box 520 illustrated in FIG. 4A. The medicine library is medicine information which is a medicine administration setting group containing preliminarily registered medicines in a medicine library database (DB). The medical staff can select and set the medicine by using the medicine library without executing complex administration setting every time.

As illustrated in FIG. 8B, the infusion pump 1 can correctly feed a medicine 171 to a patient P from a medicine bag 170 filled with the medicine 171 through a pinchcock 179, an upstream side 200A and a downstream side 200B of the infusion tube 200, and an intravenous cannula 172. The infusion pump 1 includes the main body case 2 and an assist handle 2T. The main body case 2 is integrally molded and formed with the molding resin material having chemical resistance, and provided with the splash proof structure whereby the medicine or the like can be prevented from entering inside the infusion pump 1 even when the medicine or the like is splashed and adhered. The main body case 2 is thus provided with the splash proof structure because, for example, the medicine 171 inside the medicine bag 170 located above may fall or antiseptic solution or the like used nearby may splash and adhere.

The elements disposed at the main body case 2 of the infusion pump 1 will be described. As illustrated in FIGS. 8A and 8B, the display unit 3 and an operation panel 4 are disposed at the upper portion 2A of the main body case 2. The display unit 3 is an image display device, and for example, a display device formed of a color liquid crystal and an organic EL is used. The display unit 3 is located at an upper left position of the upper portion 2A of the main body case 2 and disposed on an upper side of an access cover 5. The upper portion 2A of the main body case 2 is an upper half portion of the main body case 2. The lower portion 2B of the main body case 2 is a lower half portion of the main body case 2.

In FIG. 8B, as an example, a display field 3B for a scheduled amount (mL) of medicine administration, a display field 3C for a total amount (mL) of medicine administration, a display field 3D for electric charge history, a display field 3E for a flow rate (mL), etc. are displayed on the display unit 3. The display unit 3 may also display a warning message in addition to the above. As illustrated in FIG. 8A, the operation panel 4 is disposed on the right side of the display unit 3 at the upper portion 2A of the main body case 2, and for example, a pilot lamp 4A, a fast feed switch button 4B, a start switch button 4C, a stop switch button 4D, a menu selection button 4E, etc. are provided on the operation panel 4. A power switch button is disposed at a position different from the operation panel 4.

As illustrated in FIGS. 8A and 8B, the access cover 5 as a cover member can be opened in CS-direction and closed in CR-direction centering a rotary shaft 5A at the lower portion 2B of the main body case 2. A tube mounting section 50 and infusion tube 200 at the lower portion 2B can be covered by closing the access cover 5, and the tube mounting section 50 and infusion tube 200 can be exposed by opening the access cover 5. The infusion tube 200, which is flexible and made of thermoplastic resin such as flexible PVC, can be detachably mounted on the tube mounting section 50 at the lower portion 2B illustrated in FIG. 8B. By rotating the access cover 5 in the CR-direction to cover the tube mounting section 50, the access cover 5 laterally holds the infusion tube 200 at the tube mounting section 50 along the X-direction, particularly preferably, horizontally along the X-direction.

As illustrated in FIG. 8B, a front surface of the access cover 5 is, preferably if need be, provided with an infusion tube setting direction display 150 for clearly indicating a correct feeding direction, T-direction, at the time of setting the infusion tube 200. The infusion tube setting direction display 150 includes a medicine bag display 151 indicating a medicine bag side, a patient-side display 152 indicating a patient side, and a feeding direction display 153 clearly indicating a medicine feeding direction. As illustrated in FIG. 8B, the medicine bag display 151 is provided in order to visually confirm that the medicine bag 170 side of the infusion tube 200 is positioned on an observer's right-side portion of the access cover 5, and the patient-side display 152 is provided in order to visually confirm that the patient P side of the infusion tube 200 is positioned on the observer's left-side portion of the access cover 5. Further, the feeding direction display 153 is provided to clearly indicate the correct feeding direction, T-direction, of the medicine 171 to be fed by the infusion tube 200 set on the inner side of the access cover 5.

As illustrated in FIGS. 8A and 8B, the tube mounting section 50 is provided on the lower portion 2B side of the main body case 2 of the infusion pump 1, and the tube mounting section 50 is disposed along the X-direction below the display unit 3 and the operation panel 4. The medical staff who is a user can mount the infusion tube 200 on the tube mounting section 50 and close the access cover 5 while confirming the information on the display unit 3 at the upper portion 2A of the main body case 2. Further, the medical staff can operate the operation buttons on the operation panel 4 while confirming the information on the display unit 3 at the upper portion 2A of the main body case 2.

Next, a configuration of the syringe pump 1001 will be described with reference to FIG. 9. FIG. 9 is a perspective view illustrating the exemplary configuration of the syringe pump 1001 illustrated in FIG. 1.

The syringe pump 1001 can exchange the information with the external computer by using the rack 500 and the communication box 520 in the same manner as the infusion pump 1. The syringe pump 1001 is used in, for example, intensive care unit (ICU, CCU, NICU) or the like, and is an injection pump used for injecting, to a patient, medicines such as anticancer drug, anesthetic, chemotherapeutic agent, and nutrients and blood transfusion or the like for a long time with high accuracy. The syringe pump 1001 can select and obtain the medicine information to be used from the medicine library, for example, by using the rack 500 and communication box 520 illustrated in FIG. 4A, thereby achieving to feed the selected medicine. The medicine library is medicine information which is the medicine administration setting group containing preliminarily registered medicines in a medicine library database (DB). The medical staff can select and set the medicine by using the medicine library without executing complex administration setting every time.

Figure 9:
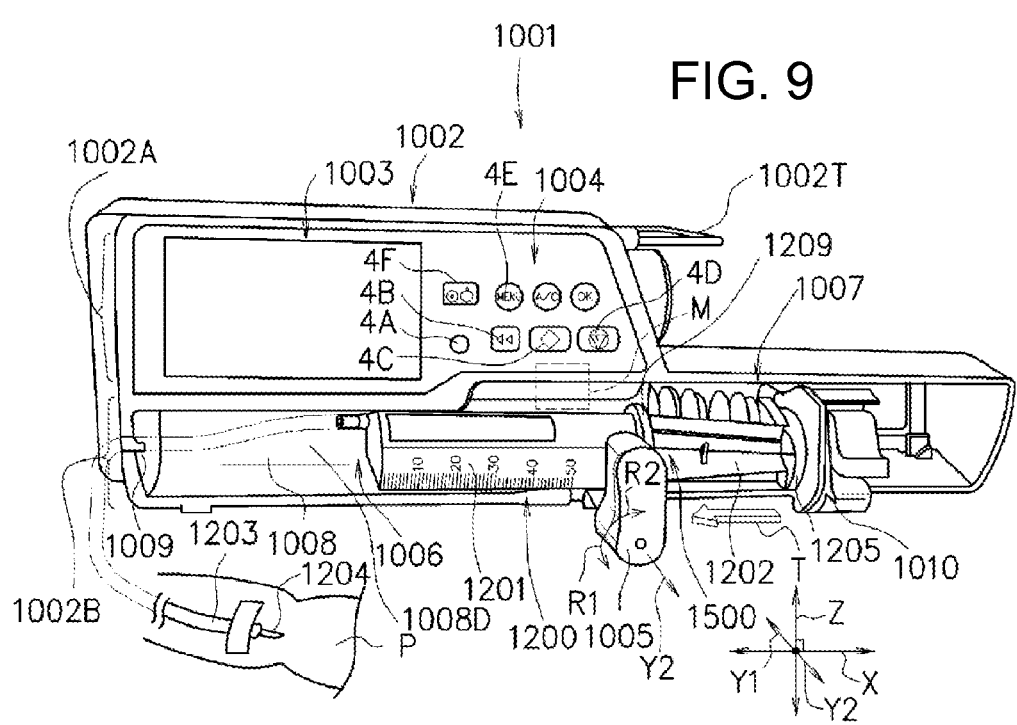
FIG. 9 is a view illustrating an exemplary configuration of a syringe pump.

As illustrated in FIG. 9, the syringe pump 1001 can be set such that a syringe main body 1201 of a syringe 1200 filled with the medicine is to be non-movable by using a clamp 1005, for example. A motor M rotates a drive shaft of a syringe pusher driving unit 1007, thereby causing a slider 1010 of the syringe pusher driving unit 1007 to push a syringe pusher 1202 of the syringe 1200 in the T-direction to correctly feed the medicine inside the syringe main body 1201 to the patient P via a tube 1203 and an intravenous cannula 1204. The syringe pump 1001 includes the main body case 1002, and the main body case 1002 is formed as a box body having liquid tightness by being integrally formed with the molding resin material having chemical resistance. By this, the splash proof structure and drip proof (water proof) structure whereby the medicine, water, etc. can be prevented from entering inside the syringe pump 1001 even when the medicine, water, etc. are splashed and adhered is provided, as described later.

As illustrated in FIG. 9, the syringe pump 1001 includes the main body case 1002 and an assist handle 1002T. A display unit 1003 and an operation panel 1004 are disposed at an upper portion 1002A of the main body case 1002. A syringe setting portion 1006, the motor M, and the syringe pusher driving unit 1007 are disposed at the lower portion 1002B of the main body case 1002. This enables the medical staff to execute medicine feeding operation from the syringe 1200 while visually confirming contents of information displayed in colors on the display unit 1003 at the upper portion 1002A of the main body case 1002. Further, the medical staff can operate the operation buttons on the operation panel 1004 while confirming the contents of information displayed in colors on the display unit 1003 of the main body case 1002.

As illustrated in FIG. 9, the display unit 1003 is a color liquid display unit (LCD) capable of displaying color graphics, or an organic EL. The display unit 1003 is provided at an upper left position of the upper portion 1002A of the main body case 1002, and disposed on the upper side of the syringe setting portion 1006 and syringe pusher driving unit 1007. The operation panel 1004 is disposed on the right side of the display unit 1003 at the upper portion 1002A of the main body case 1002, and according to the example illustrated, a pilot lamp 4A, a fast feed switch button 4B, a start switch button 4C, a stop switch button 4D, a menu selection button 4E, etc. are provided as the operation buttons on the operation panel 1004.

The upper portion 1002A of the main body case 1002 illustrated in FIG. 9 is an upper half portion of the main body case 1002. The lower portion 1002B of the main body case 1002 is a lower half portion of the main body case 1002. The syringe setting portion 1006 and syringe pusher driving unit 1007 are arranged along the X-direction. At the syringe setting portion 1006, a syringe 1200 having a required capacity selected from among plural kinds of syringes having different capacity can be fitted and detachably mounted.

The syringe setting portion 1006 includes a housing portion 1008 to house the syringe main body 1201, a clamp 1005, and a main body flange gripping portion 1500 for fitting and gripping the main body flange 1209 of the syringe 1200. The housing portion 1008 includes a recessed syringe main body holding portion 1008D. A tube fixing portion 1009 for detachably clipping the tube 1203 is formed on a wall portion at a left-side end portion of the housing portion 1008. The tube fixing portion 1009 is a groove portion where the tube 1203 is partly clipped and fixed as illustrated in FIG. 9.

In FIG. 9, when the medical staff operates the clamp 1005 to detach the syringe 1200 from the syringe setting portion 1006, the clamp 1005 is separated from an outer peripheral surface of the syringe main body 1201 by, for example, pulling the clamp 1005 in the Y2-direction (frontward direction) against force of a spring not illustrated and rotating the same in R1-direction by 90 degrees. In this manner, fixation of the syringe main body 1201 by the clamp 1005 is released and can be taken out from the syringe main body holding portion 1008D of the housing portion 1008, and also the tube 1203 can be detached from the inside of the tube fixing portion 1009. Further, when the syringe 1200 is set to the housing portion 1008 of the syringe setting portion 1006 by operating the clamp 1005, the syringe main body 1201 is housed inside the syringe main body holding portion 1008D of the housing portion 1008, and also can be fixed by pulling the clamp 1005 in the Y2-direction against force of the spring not illustrated, and rotating the same in R2-direction by 90 degrees, and then returning the same in Y1-direction by the force of the spring.

As illustrated in FIG. 9, when the syringe main body 1201 is housed and set inside the syringe main body holding portion 1008D of the housing portion 1008, the syringe pusher 1202 is disposed inside the syringe pusher driving unit 1007. This syringe pusher driving unit 1007 includes the slider 1010. When the motor M is driven by a command from a control unit, the slider 1010 gradually pushes a pusher flange 1205 of the syringe pusher 1202 relatively in T-direction with respect to the syringe main body 1201. By this, the medicine inside the syringe main body 1201 can be fed to the patient P via the tube 1203 and intravenous cannula 1204 with high accuracy for a relatively long time.

Next, a description will be given for a configuration in which the medical staff detachably mounts the infusion pump 1 illustrated in FIGS. 8A and 8B or the syringe pump 1001 illustrated in FIG. 9 to the first mounting section C1, second mounting section C2, and third mounting section C3 illustrated in FIGS. 2 and 3 like the mounting example illustrated in FIG. 1, for example.

Figure 11:
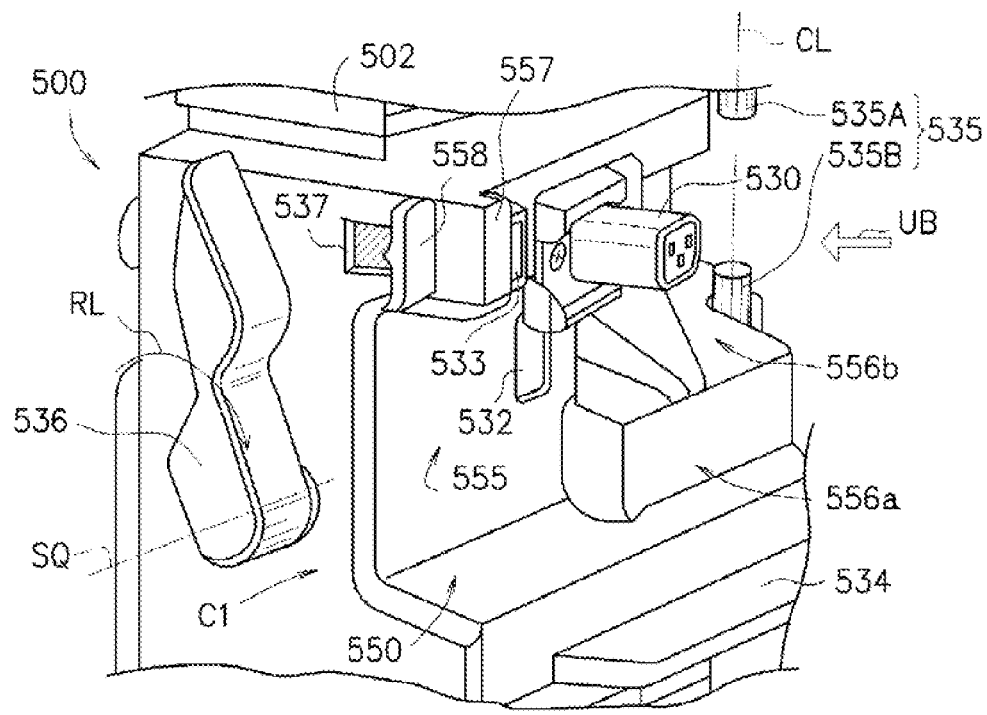
FIG. 11 is a perspective view illustrating the first mounting section viewed from CN-direction in FIG. 10A.

FIG. 10A is a perspective view illustrating the first mounting section C1 out of the first mounting section C1, second mounting section C2, and third mounting section C3 illustrated in FIG. 2 as the representative of the first mounting section C1, second mounting section C2, and third mounting section C3. FIG. 10B is a perspective view of the first mounting section C1 illustrated in FIG. 10A viewed from the front side. FIG. 11 is a perspective view illustrating the first mounting section C1 viewed from CN-direction in FIG. 10A.

The main body case 2 of the infusion pump 1 illustrated in FIGS. 8A and 8B and the main body case 1002 of the syringe pump 1001 illustrated in FIG. 9 are common in having the same outer shape except for a portion. Therefore, the infusion pump 1 and the syringe pump 1001 can be commonly mounted on any one of the first mounting section C1, second mounting section C2, and third mounting section C3 of the rack 500.

The first mounting section C1 illustrated in FIGS. 10A and 10B includes the outlet terminal 530 for power connection, lock mechanism 531, IrDA 532, pusher 533, tray 534 as a supporting projected portion, supporting portion 535, operation lever 536, and indicator 537 (see FIG. 11). The first mounting section C1 will be further described with reference to FIGS. 10A and 10B. Note that the second mounting section C2 and the third mounting section C3 illustrated in FIG. 2 are same as the configuration of the first mounting section C1.

Figure 12:
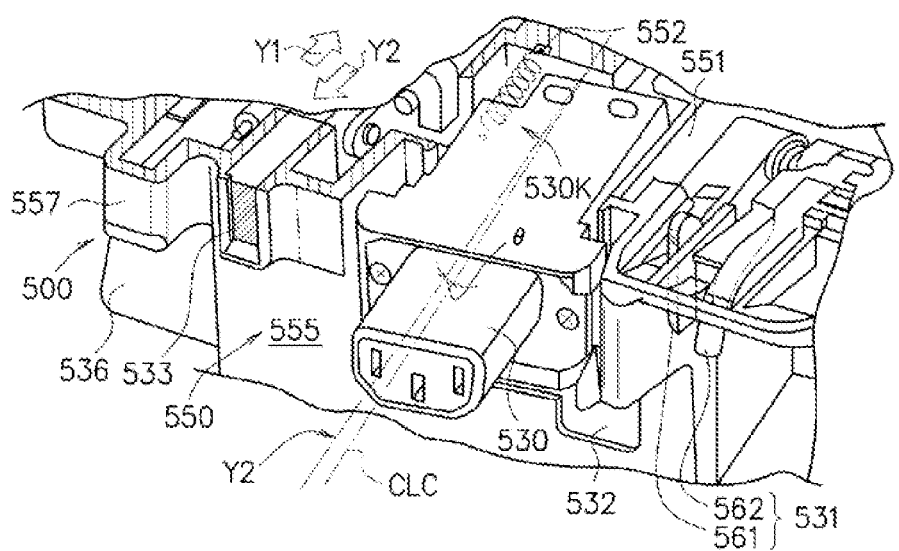
FIG. 12 is a perspective view illustrating a configuration in the vicinity of an outlet terminal for power source connection, viewed from the UB-direction illustrated in FIG. 11.

FIG. 12 is a perspective view illustrating an exemplary configuration in the vicinity of the outlet terminal 530 for power source connection, viewed from UB-direction illustrated in FIG. 11. As illustrated in FIG. 12, the outlet terminal 530 for power source connection is housed and held in a mounting base 551. A spring 552 is disposed inside the mounting base 551, and interposed between a rear end portion 530K of the outlet terminal 530 and the mounting base 551.

The mounting base 551 is fixed by being embedded in a front surface portion 550 of the first mounting section C1. The outlet terminal 530 for power source connection is disposed in a projecting manner in CLC-direction at a predetermined inclination angle θ, for example, at the angle of 5 degrees, with respect to the Y2-direction (front-rear direction) of the rack 500 by force of the spring 552. In other words, the Y2-direction of the rack 500 is vertical to the front surface portion 550 of the first mounting section C1, but the outlet terminal 530 for power source connection is obliquely projected along the CLC-direction from the front surface portion 550 of the first mounting section C1. The outlet terminal 530 for power source connection can be moved back to the rear side inside the mounting base 551 by being pushed along the CLC-direction against force of the spring 552. With this configuration, the outlet terminal 530 for power source connection can be surely and smoothly connected to an outlet receiving portion of the infusion pump 1 later described or an outlet receiving portion of the syringe pump 1001 in a detachable manner.

The front surface portion 550 of the first mounting section C1 illustrated in FIGS. 11 and 12 is formed between the upper wall CW1 and lower wall CV1 of the first mounting section C1 illustrated in FIG. 10A. As illustrated in FIG. 10A, the front surface portion 550 includes a flat portion 555, a projected portion 556a, and a recessed portion 556b. The flat portion 555 is positioned on the left side and the projected portion 556a and recessed portion 556b are positioned on the right side. The flat portion 555, projected portion 556a, and recessed portion 556b of the front surface portion 550 are formed conforming to a form of a projection and recess on the rear surface portion side of the infusion pump 1 illustrated in FIGS. 8A and 8B and the form of the projection and recess on the rear surface portion side of the syringe pump 1001 illustrated in FIG. 9.

As illustrated in FIGS. 10A and 10B, the outlet terminal 530 for power source connection, the lock mechanism 531, the pusher 533, the upper post 535A of the supporting portion 535, an abutting portion for positioning 557, and a stopper 558 are disposed on the upper wall CW1. The IrDA 532 is the flat portion 555 and disposed at a position below the outlet terminal 530. The lower post 535B of the supporting portion 535 is disposed on the lower wall CV1. The upper post 535A and lower post 535B of the supporting portion 535 are positioned rightmost of the first mounting section C1 as illustrated in FIGS. 10A and 10B, and the pusher 533 and the stopper 558 are positioned leftmost of the first mounting section C1.

As illustrated in FIG. 10A, the tray 534 is a plate-like supporting projected portion formed in a projecting manner horizontally in the Y2-direction (front side). When the infusion pump 1 illustrated in FIGS. 8A and 8B or the syringe pump 1001 illustrated in FIG. 9 is mounted on and detached from the first mounting section C1, the tray 534 serves to support the lower portion of the infusion pump 1 or the lower portion of the syringe pump 1001 such that the infusion pump 1 or the syringe pump 1001 does not fall from the first mounting section C1. With this configuration, the infusion pump 1 or the syringe pump 1001 can be prevented from falling from the rack 500 at the time of mounting or detaching, and safety can be secured.

When the infusion pump 1 illustrated in FIGS. 8A and 8B or the syringe pump 1001 illustrated in FIG. 9 is mounted and properly fixed to the first mounting section C1, the abutting portion for positioning 557 illustrated in FIG. 11 has a function to mount the pump to the first mounting section C1 at a predetermined accurate posture by being abutted on the rear surface of the infusion pump 1 illustrated in FIGS. 8A and 8B or the rear surface portion of the syringe pump 1001 illustrated in FIG. 9. The stopper 558 illustrated in FIG. 11 restricts a rotary angle of the operation lever 536 at the time of rotating the operation lever 536 in RL-direction.

The lock mechanism 531 illustrated in FIG. 12 is configured to detachably lock the pole clamp for pumps (later described) for clamping the infusion pump 1 or the syringe pump 1001. The IrDA 532 can exchange information with the IrDA (not illustrated) provided on the rear surface portion side of the infusion pump 1 or the syringe pump 1001 by executing optical radio communication. When the medical staff rotates the operation lever 536 in the RL-direction illustrated in FIG. 11, the pusher 533 illustrated in FIGS. 11 and 12 is projected in the Y2-direction by the amount of predetermined stroke STC from a housed state illustrated in FIGS. 14A and 14B. When the pusher 533 is projected, the pusher 533 can push out the rear surface portion side of the infusion pump 1 or syringe pump 1001 that has been mounted. In this manner, detachment of the infusion pump 1 or syringe pump 1001 from the first mounting section C1 can be easily executed by this projecting operation of the pusher 533.

Figure 13A:
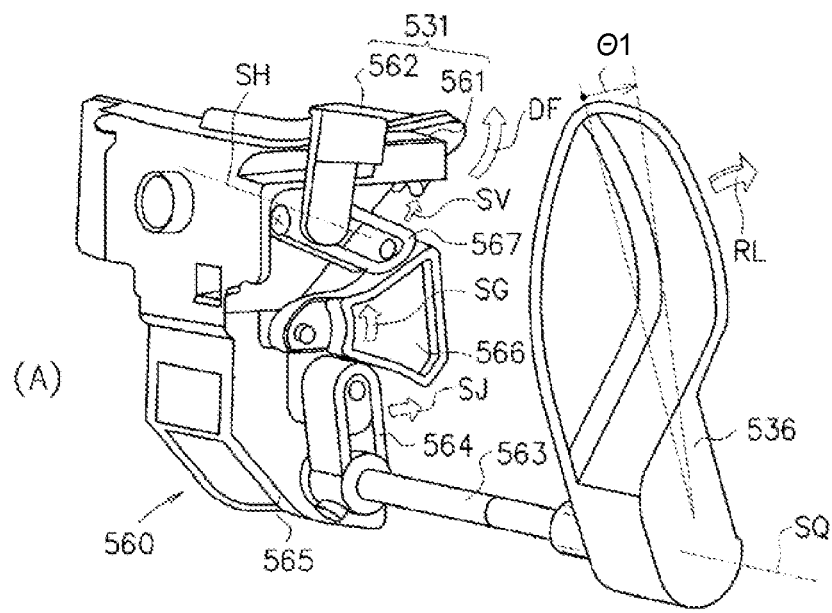
FIG. 13A is a perspective view illustrating an exemplary configuration of a first operation mechanism for interlocking an operation lever with a lock mechanism.
Figure 13B:
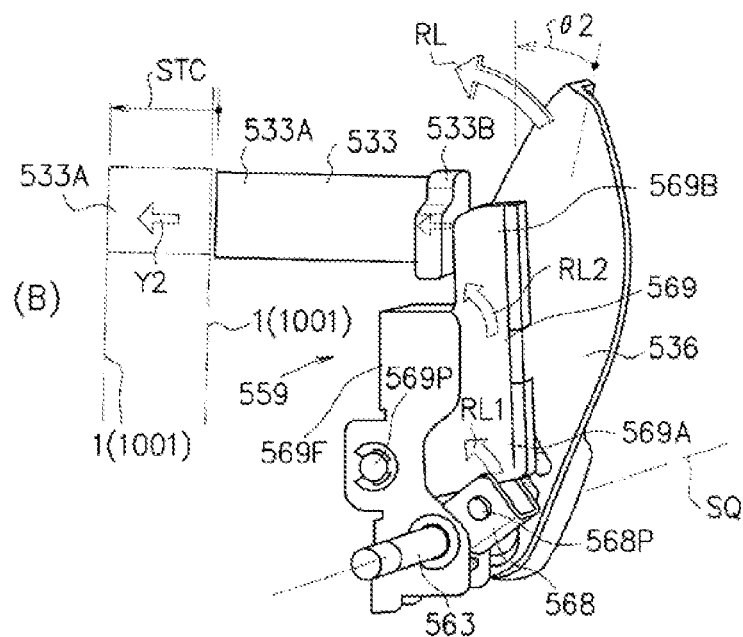
FIG. 13B is a perspective view illustrating an exemplary configuration of a second operation mechanism for interlocking the operation lever with a pusher.

FIG. 13A is a view illustrating an exemplary configuration of a first operation mechanism 560 to interlock the operation lever 536 with the lock mechanism 531. FIG. 13B is a view illustrating an exemplary configuration of a second operation mechanism 559 to interlock the operation lever 536 with the pusher 533. FIG. 14A is a diagram illustrating a state in which the pusher 533 is housed inside a housing portion 533N. FIG. 14B is a diagram illustrating a state in which the pusher 533 is projected from the housing portion 533N by the amount of predetermined stroke STC.

The first operation mechanism 560 illustrated in FIG. 13A has a function to lift a second claw portion 562 of the lock mechanism 531 in DF-direction by the medical staff rotating the operation lever 536 in the RL-direction around a rotary center shaft SQ. A first claw portion 561 is a temporary fixing member to temporarily fix the infusion pump 1 (or syringe pump 1001) to the rack 500 side, and the second claw portion 562 is a main fixing member to properly fix the infusion pump 1 (or syringe pump 1001) to the rack 500 side. Temporary fixation is also referred to as pre-lock and proper fixation is also referred to as final-lock.

As illustrated in FIG. 13A, a shaft portion 563 of the operation lever 536 is mounted on a frame 565 and can be rotated in the RL-direction. The shaft portion 563 is mounted with a first cam 564. A second cam 566 and a third cam 567 are mounted with the frame 565. The first cam 564, the second cam 566, and the third cam 567 sequentially contact each other. The third cam 567 is connected to the second claw portion 562 of the lock mechanism 531 by using a connecting shaft, and therefore, the third cam 567 and second claw portion 562 can be integrally rotated around the rotary center shaft SH.

When the medical staff rotates the operation lever 536 in the RL-direction by a predetermined angle θ1 such as 10 degrees, the first cam 564 is rotated in SJ-direction and the second cam 566 is rotated in SG-direction to be lifted up. When the second cam 566 is lifted up, the third cam 567 is lifted in SV-direction. As a result, the second claw portion 562 can be lifted in DF-direction. The second claw portion 562 for proper fixation can surely release a state in which the second claw portion 562 is engaged with the rear surface portion side of the infusion pump 1 or the syringe pump 1001 by lifting the second claw portion 562 in the DF-direction. However, even when proper fixation by the second claw portion 562 is released, engagement by the first claw portion 561 is not released.

Next, the second operation mechanism 559 illustrated in FIG. 13B has a function to push out the pusher 533 in the Y2-direction by an amount of predetermined stroke STC when the medical staff rotates the operation lever 536 around the rotary center shaft SQ in the RL-direction by a predetermined rotary angle θ2, for example, 30 degrees. The shaft portion 563 of the operation lever 536 is mounted on a frame 569F to fix a link member 568. The link member 568 is connected to a lower end portion 569A of the operation member 569 by using a pin 568P. An upper end portion 569B of the operation member 569 is made to contact a rear end portion 533B of the pusher 533. The operation member 569 is rotatable at the frame 569F by using a pin 569P.

With this configuration, when the medical staff rotates the operation lever 536 illustrated in FIG. 13B in the RL-direction, the link member 568 is rotated in RL1-direction, and therefore, the other operation member 569 is lifted in RL2-direction. Therefore, the medical staff rotates the operation lever 536 in the RL-direction by the predetermined angle θ2, thereby projecting a tip 533A of the pusher 533 in the Y2-direction by the amount of predetermined stroke STC as illustrated in FIGS. 14A and 14B. The tip 533A of the pusher 533 is projected in the Y2-direction by the amount of predetermined stroke STC. Due to this, the medical staff can easily detach the infusion pump 1 or syringe pump 1001 from the first mounting section C1 by pushing out, in the Y2-direction (frontward), the rear surface portion of the infusion pump 1 or the rear surface portion of the syringe pump 1001 mounted on the first mounting section C1 in FIG. 11, for example.

As described above, in FIGS. 13A and 13B, the second claw portion 562 for proper fixation of the lock mechanism 531 is lifted in the DF-direction by rotating the operation lever 536 in the RL-direction by the predetermined angle θ1. Consequently, the second claw portion 562 can surely release the state in which the second claw portion 562 is engaged with the rear surface portion of the infusion pump 1 or the syringe pump 1001. Further, temporary fixation of the infusion pump 1 by the first claw portion 561 is not released even when proper fixation by the second claw portion 562 is released. However, when the medical staff rotates the operation lever 536 in the RL-direction by the predetermined angle θ2, the rear surface portion of the infusion pump 1 or the rear surface portion of the syringe pump 1001 mounted on, for example, the first mounting section C1 in FIG. 11 is forcibly pushed out in the Y2-direction, thereby releasing temporary fixation by the first claw portion 561 of the infusion pump 1 or the syringe pump 1001. Therefore, the infusion pump 1 or syringe pump 1001 can be easily mounted and detached.

Figure 15A:
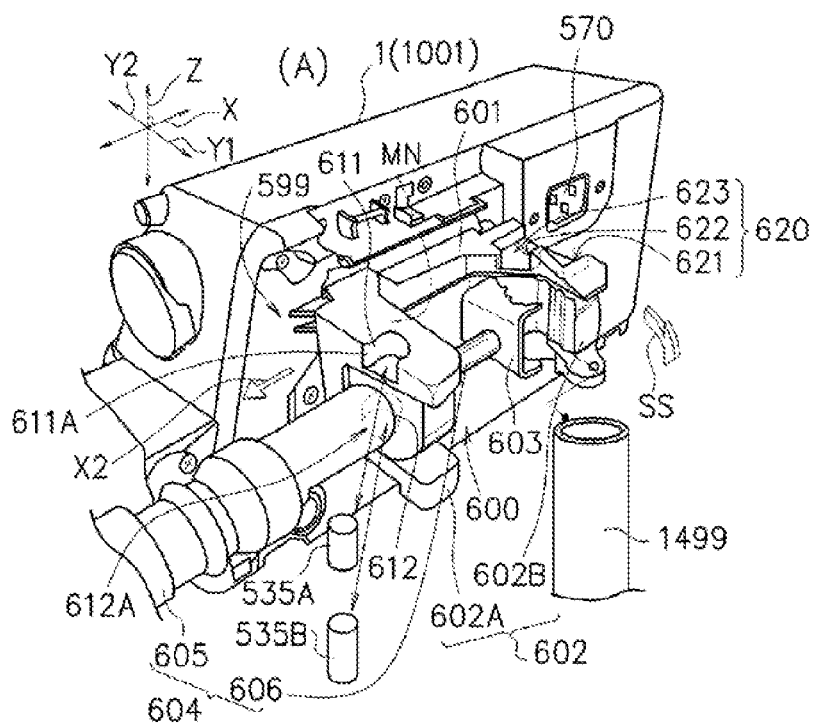
FIG. 15A is a left rear perspective view illustrating the rear surface portion side of the infusion pump illustrated in FIGS. 8A and 8B.
Figure 15B:
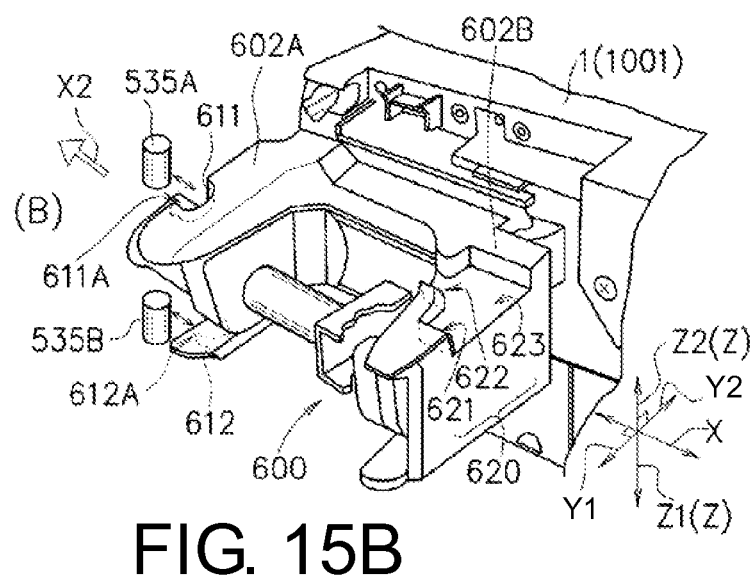
FIG. 15B is a right rear perspective view illustrating the infusion pump of FIG. 15A.

Next, FIGS. 15A and 15B are views illustrating the rear surface portion side of the infusion pump 1 illustrated in FIGS. 8A and 8B. The rear surface portion side of the syringe pump 1001 illustrated in FIG. 9 has a substantially similar form, and therefore, the configuration of the rear surface portion side of the infusion pump 1 will be representatively described.

As illustrated in FIGS. 15A and 15B, the rear surface portion side of the infusion pump 1 includes a pole clamp 600 for a pump and an outlet receiving portion 570. The outlet receiving portion 570 is provided to electrically and mechanically connect the outlet receiving portion 570 with the outlet terminal 530 by detachably inserting the outlet terminal 530 for power source connection illustrated in FIGS. 10A and 10B.

The pole clamp 600 for the pump is detachably mounted on the rear surface portion of the infusion pump 1 by using an attaching portion 599 preliminarily provided. The pole clamp 600 is used in the case of detachably mounting the infusion pump 1 illustrated in FIGS. 8A and 8B or the syringe pump 1001 illustrated in FIG. 9 directly to a different pump mounting pole 1499 without using the rack 500 illustrated in FIG. 1.

The configuration of the pole clamp 600 for the pump illustrated in FIGS. 15A and 15B is different from the configuration of the pole clamp 400 for the rack 500 illustrated in FIGS. 5, 6, and 7. The pole clamp 600 for the pump includes a plastic base portion 601, a metal-made fixing tool 602 for mounting, a metal-made moving tool 603 for mounting, and an operating unit 604.

The base portion 601 can be mounted by being fitted to the attaching portion 599 provided at the rear surface portion of the infusion pump 1. The fixing tool 602 is fixed to the base portion 601. The fixing tool 602 includes a first projected portion 602A and a second projected portion 602B disposed apart from and facing the first projected portion 602A. A part of the operating unit 604 is fixed to the first projected portion 602A and the operating unit 604 includes a rotary portion 605 and a moving member 606. The moving tool 603 is fixed to a tip of the moving member 606. The operating unit 604 is disposed along the X-direction, and the medical staff rotates the rotary portion 605, thereby moving the moving tool 603 of the moving member 606 along the X-direction and clipping the pole 1499 between the moving tool 603 and the second projected portion 602B. By this, the infusion pump 1 or syringe pump 1001 can be detachably held.

As illustrated in FIGS. 15A and 15B, the first projected portion 602A includes a first insertion hole 611 and a second insertion hole 612. The first insertion hole 611 and second insertion hole 612 respectively include opening portions 611A, 612A opened in X2-direction. The opening portion 611A and opening portion 612A are formed in order that the upper post 535A and lower post 535B are surely and easily inserted into the first insertion hole 611 and second insertion hole 612 respectively from the side.

The first insertion hole 611 is formed on an upper surface side of the first projected portion 602A, the second insertion hole 612 is formed on a lower surface side of the first projected portion 602A, and the first insertion hole 611 and second insertion hole 612 are disposed along a center shaft MN. In the first insertion hole 611, the upper post 535A of the supporting portion 535 illustrated in FIGS. 15A, 15B, 10A, and 10B is detachably inserted. In the same manner, the lower post 535B of the supporting portion 535 illustrated in FIGS. 15A, 15B, 10A, and 10B is detachably inserted into the second insertion hole 612. In other words, the rotary center shaft CL illustrated in FIGS. 10A and 10B coincides with the center shaft MN illustrated in FIG. 15A.

On the other hand, an engagement portion 620 is provided on the upper surface side of the second projected portion 602B. The engagement portion 620 can be engaged individually with each of the first claw portion 561 and the second claw portion 562 of the lock mechanism 531 illustrated in FIGS. 14A and 14B. The engagement portion 620 includes a first stepped portion 621, a second stepped portion 622, and a recessed portion 623.

The recessed portion 623 is formed so as to be recessed in the Z1-direction (downward), and the first stepped portion 621 and second stepped portion 622 are formed at the end portion of the recessed portion 623 so as to be projected in the Z2-direction. The first stepped portion 621 is formed adjacent to the second stepped portion 622, but the first stepped portion 621 is more deviated in the Y1-direction (rearward) than the second stepped portion 622. In other words, the first stepped portion 621 is formed more in the Y1-direction and the second stepped portion 622 is formed more in the Y2-direction.

Figure 16A:
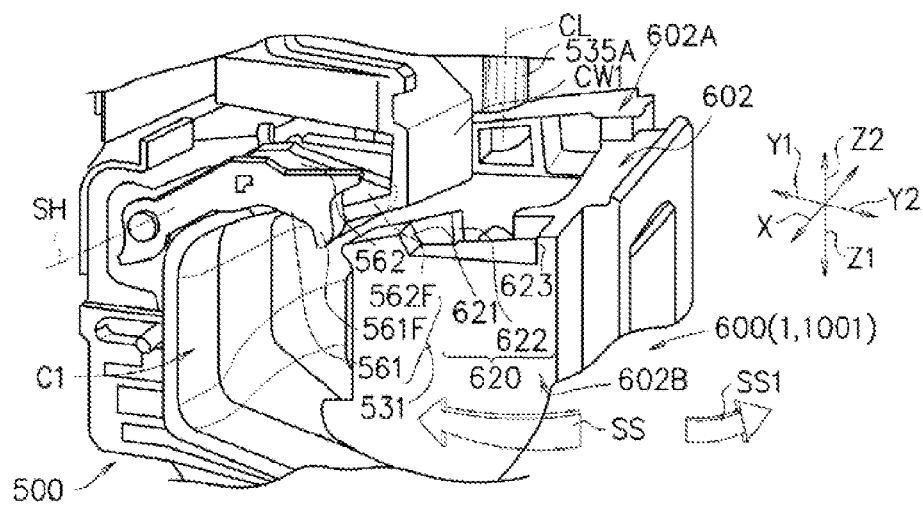
FIG. 16A is a perspective view illustrating a state before a first claw portion and a second claw portion are respectively engaged with a first stepped portion and a second stepped portion.
Figure 16B:
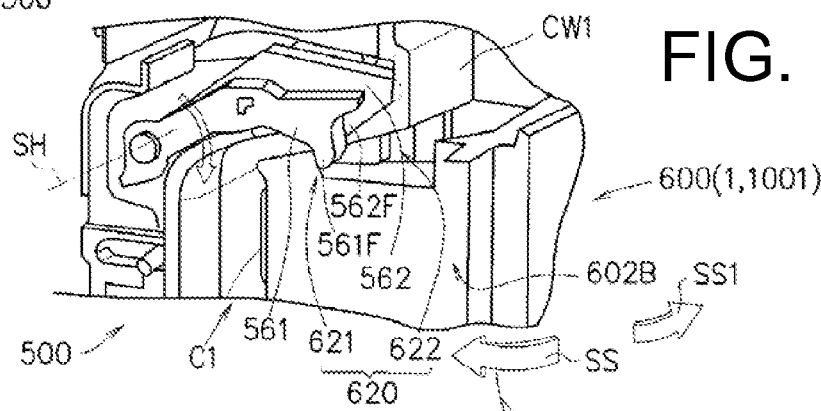
FIG. 16B is a view illustrating a state in which an infusion pump (or syringe pump) is temporarily fixed to the first mounting section side by only the first claw portion being engaged with the first stepped portion but the second claw portion not being engaged with the second stepped portion.
Figure 16C:
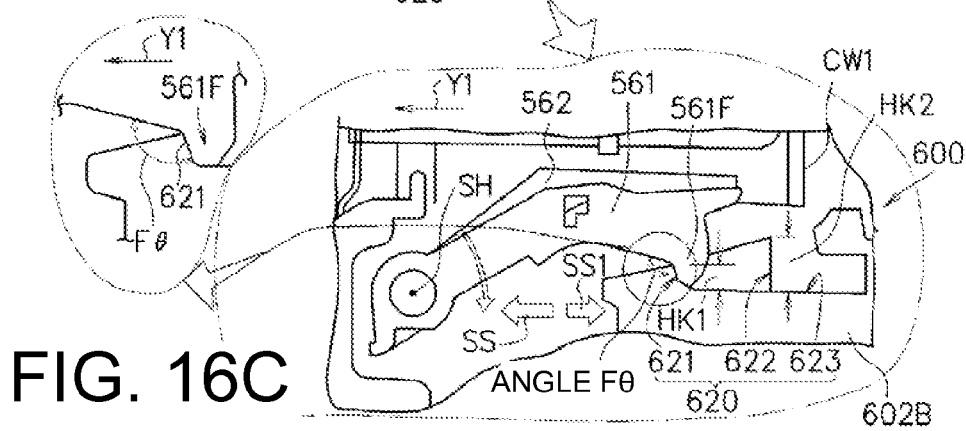
FIG. 16C is a side perspective view of the temporarily fixed engagement shown in FIG. 16B.

As illustrated in FIG. 16C, a forming height HK1 of the first stepped portion 621 formed from the recessed portion 623 in the Z2-direction is set smaller than a forming height HK2 of the second stepped portion 622 formed from the recessed portion 623 in the Z2-direction. With this configuration, the temporary fixing state in which the first claw portion 561 is engaged with the first stepped portion 621 can be easily released, compared to the proper fixing state in which the second claw portion 562 is engaged with the second stepped portion 622.

FIGS. 16A to 16C and 17A to 17B are views illustrating a state in which the first claw portion 561 and second claw portion 562 of the lock mechanism 531 illustrated in FIGS. 14A and 14B are respectively engaged with the first stepped portion 621 and second stepped portion 622 of the second projected portion 602B. FIG. 16A is a perspective view illustrating a state before the first claw portion 561 and second claw portion 562 are respectively engaged with the first stepped portion 621 and second stepped portion 622. FIG. 16B is a view illustrating a state in which the infusion pump 1 (or syringe pump 1001) is temporarily fixed to the first mounting section C1 side by only the first claw portion 561 being engaged with the first stepped portion 621 but the second claw portion 562 not being engaged with the second stepped portion 622. FIG. 16C is a side perspective view of the state shown in FIG. 16B. FIG. 17A is a view illustrating the proper fixing state in which only the second claw portion 562 is engaged with the second stepped portion 622. In other words, the state in which the infusion pump 1 (or syringe pump 1001) is properly fixed to the first mounting section C1 side by the first claw portion 561 being separated from the first stepped portion 621 and not engaged with the first stepped portion 621. FIG. 17B is a side perspective view of the fixing state shown in FIG. 17A As illustrated in FIGS. 16A to 16C and 17A, the first claw portion 561 includes an L-shape tip 561F and the second claw portion 562 includes an L-shape tip 562F. As illustrated in FIG. 16A, in the case where the medical staff mounts the infusion pump 1 on the first mounting section C1 of the rack 500 by rotating the pump around the rotary center shaft CL in the SS-direction while holding the infusion pump 1 including the pole clamp 600 illustrated in FIGS. 15A and 15B, the tip 561F of the first claw portion 561 is moved toward the first stepped portion 621 as illustrated in FIG. 16A and engaged first with the first stepped portion 621 as illustrated in FIGS. 16B and 16C. By this, the infusion pump 1 is temporarily fixed to the first mounting section C1 side by engagement of the tip 561F of the first claw portion 561 with the first stepped portion 621.

However, the L-shape tip 561F of the first claw portion 561 has a forming angle Fθ larger than 90 degrees as illustrated in FIG. 16C, and further the first stepped portion 621 is formed in an inclined manner toward Y1. Accordingly, as illustrated in FIGS. 16B and 16C, when the medical staff pulls the pole clamp 600 in SS1-direction together with the infusion pump 1 while the infusion pump 1 is temporarily fixed to the first mounting section C1, the tip 561F of the first claw portion 561 is easily lifted and detached from the first stepped portion 621. Therefore, the infusion pump 1 can be easily and smoothly taken out in the SS1-direction.

Again, as illustrated in FIGS. 16B and 16C, when the medical staff further rotates the infusion pump 1 around the rotary center shaft CL in the SS-direction while holding the infusion pump 1 illustrated in FIGS. 15A and 15B, the second claw portion 562 is engaged with the second stepped portion 622 as illustrated in FIGS. 17A and 17B. By this, the infusion pump 1 can be properly fixed by engagement of the tip 562F of the second claw portion 562 with the second stepped portion 622.

Note that the tip 562F of the second claw portion 562 and the second stepped portion 622 are formed such that the tip 562F of the second claw portion 562 is not lifted from the second stepped portion 622 even when the pole clamp 600 is pulled in the SS1-direction together with the infusion pump 1. In other words, the tip 562F has a forming angle Gθ smaller than 90 degrees, and further, the second stepped portion 622 is formed perpendicular to the Z2-direction. Therefore, the tip 562F of the second claw portion 562 is configured to be hardly detached from the second stepped portion 622, and the infusion pump 1 cannot be detached in the SS1-direction while the infusion pump 1 is properly fixed.

Next, FIGS. 18A and 18B are views illustrating a state in which the infusion pump 1 is mounted on the first mounting section C1 of the rack 500 by rotating the infusion pump 1 around the supporting portion 535 in the SS-direction. Note that the syringe pump 1001 can be mounted on the first mounting section C1 of the rack 500 the same way as the infusion pump 1.

As illustrated in FIG. 18A, the medical staff holds the right side of the infusion pump 1 with the right hand and the left side of the infusion pump 1 with the left hand, and fits the upper post 535A into the first insertion hole 611 on the infusion pump 1 side and further fits the lower post 535B into the second insertion hole 612 on the infusion pump 1 side. In this state, the outlet receiving portion 570 of the infusion pump 1 faces the outlet terminal 530 for power source connection.

The outlet receiving portion 570 of the infusion pump 1 thus faces the outlet terminal 530 on the first mounting section C1 side because the outlet terminal 530 is disposed in a projecting manner in the CLC-direction at the predetermined inclination angle θ with respect to the Y2-direction of the rack 500 by force of the spring 552 as illustrated in FIG. 12. The CLC-direction is a rotary direction of the outlet receiving portion 570 of the infusion pump 1 around the rotary center shaft CL.

With this configuration, the outlet receiving portion 570 of the infusion pump 1 can directly face the outlet terminal 530 on the first mounting section C1 side at the time of mounting the infusion pump 1 on the first mounting section C1, and as illustrated in FIGS. 18A and 18B, the outlet terminal 530 on the first mounting section C1 side can be surely and smoothly fitted into the outlet receiving portion 570 of the infusion pump 1 to be electrically connected only by rotating the infusion pump 1 around the rotary center shaft CL in the SS-direction.

Figure 19A:
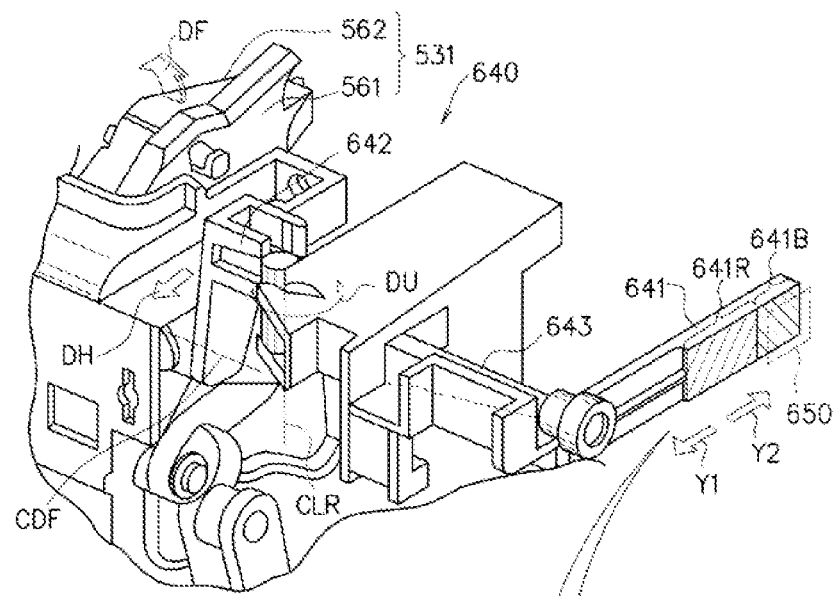
FIG. 19A is a top end perspective view illustrating an operation mechanism of an indicator.
Figure 19B:
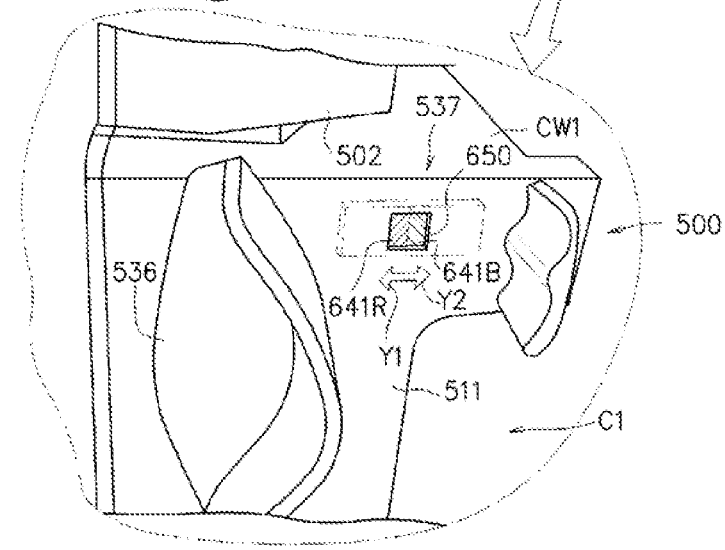
FIG. 19B is a side perspective view illustrating a visual indication that the infusion pump is temporarily or properly fixed to the medical device rack.

FIG. 19A is a perspective view illustrating an operation mechanism 640 of the indicator 537. FIG. 19B is a side perspective view illustrating a visual indication that the infusion pump 1 is temporarily or properly fixed to the medical device rack 500.

The operation mechanism 640 of the indicator 537 illustrated in FIGS. 19A and 19B is disposed inside the first mounting section C1 of the rack 500, and includes a slide plate 641, a link member 642, and a connecting member 643. When the second claw portion 562 which is the main fixing member is lifted in the DF-direction, the link member 642 is rotated in DH-direction and the connecting member 643 is rotated around a center shaft CLR in DU-direction. This causes the slide plate 641 to slide in the Y2-direction by an amount of a predetermined stroke.

As illustrated in FIGS. 17A and 17B, in the proper fixing state in which the second claw portion 562 which is the main fixing member is engaged with the second stepped portion 622, the second claw portion 562 is not lifted in the DF-direction and the infusion pump 1 (or syringe pump 1001) is properly fixed to the rack 500 side. In this case, a window 650 of the indicator 537 displays a blue region 641B of the slide plate 641 in order to indicate this proper fixing state. Therefore, the medical staff can visually confirm, by checking this green region 641B, that the infusion pump 1 is safely and properly fixed to the first mounting section C1. Meanwhile, in the case where the infusion pump 1 (or syringe pump 1001) is not yet mounted on the rack 500, the window 650 of the indicator 537 also displays the blue region 641B of the slide plate 641 in order to indicate such a non-mounted state. By this, the non-mounted state of the infusion pump 1 can be visually checked. The blue region 641B of the slide plate 641 indicates the proper fixing state in which the infusion pump 1 is surely and properly fixed. To indicate the proper fixing state, character indication, symbol mark indication, or the like may also be displayed at the window 650 of the indicator 537 instead of displaying the blue region 641B.

On the other hand, in the temporary fixing state in which the second claw portion 562 is lifted in the DF-direction and the first claw portion 561 which is the temporary fixing member is engaged with the first stepped portion 621 as illustrated in FIGS. 16A to 16C, the infusion pump 1 (or syringe pump 1001) is temporarily fixed to the rack 500 side. In this case, the second claw portion 562 is lifted in the DF-direction around a center shaft CDF as illustrated in FIG. 19A, and therefore, the link member 642 is rotated in the DH-direction and the connecting member 643 is rotated around the center shaft CLR in the DU-direction. This causes the slide plate 641 to slide in the Y2-direction by an amount of a predetermined stroke. By this, the slide plate 641 slides in the Y2-direction and a red region 641R of the slide plate 641 is displayed at the window 650 of the indicator 537, by a color different from the blue color that indicates the proper fixing state or the non-mounted state. The red region 641R of the slide plate 641 indicates the temporary fixing state in which the infusion pump 1 is surely and temporarily fixed.

This enables the medical staff to visually confirm that the infusion pump 1 (or syringe pump 1001) is temporarily fixed to the rack 500 by checking the red region 641R of the slide plate 641 displayed at the indicator 537, which is effective in a safety aspect. Thus, the medical staff can visually check whether the infusion pump (or syringe pump 1001) is temporarily fixed or properly fixed to the first mounting section C1 (second mounting section C2, third mounting section C3) as the indicator 537 is provided, and can safely execute mounting work and detaching work for the infusion pump (or syringe pump 1001).

To indicate the temporary fixing state, character indication, symbol mark indication, or the like may also be displayed at the window 650 of the indicator 537 instead of displaying the red region 641R.

Figure 20A:
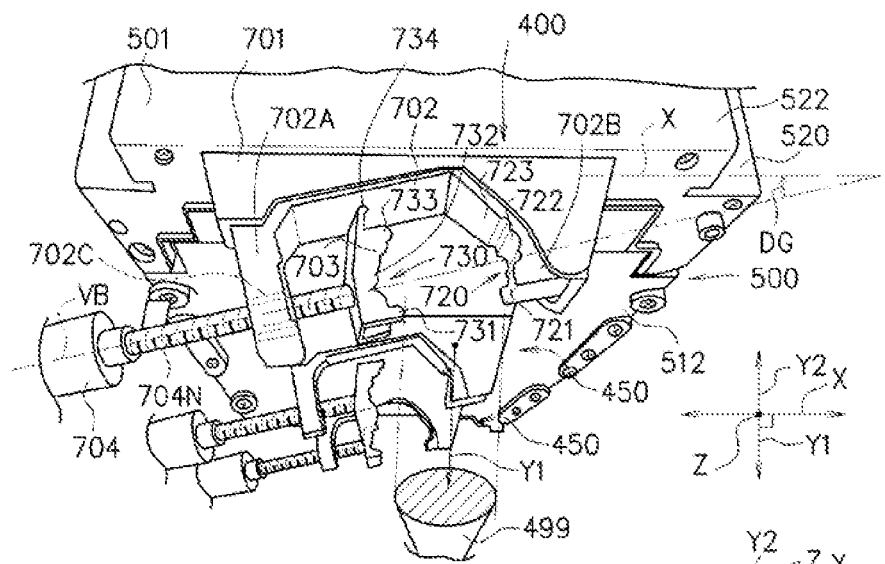
FIG. 20A is a perspective view illustrating a configuration of three pole clamps of the rack illustrated in FIG. 5, obliquely viewed from above.
Figure 20B:
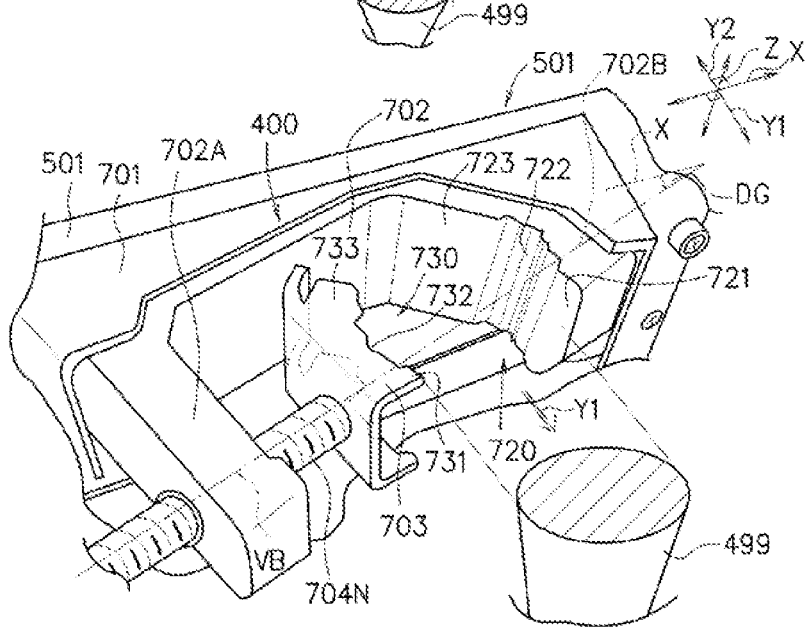
FIG. 20B is a perspective view illustrating a configuration of one of the three pole clamps shown in FIG. 20A, obliquely viewed from above

FIG. 20A is a perspective view illustrating configurations of two pole clamps 400 of the rack 500 and one pole clamp 400 for the communication box 520 illustrated in FIG. 5, obliquely viewed from above. FIG. 20B is a perspective view illustrating one pole clamp 400.

Referring to FIGS. 20A, 20B, and 5, the pole clamp 400 includes a plastic base portion 701, a metal-made fixing tool 702 for mounting, a metal-made moving tool 703 for mounting, and an operating unit 704. The base portion 701 is fixed at a center position of the rear case 512 of the rack 500 in the lateral direction (X-direction). The fixing tool 702 is fixed to the base portion 701, and the fixing tool 702 includes a first projected portion 702A and a second projected portion 702B disposed apart from and facing the first projected portion 702A. A male screw 704N of the operating unit 704 is engaged with a female screw 702C of the first projected portion 702A, and the male screw 704N has a tip mounted on the moving tool 703. The medical staff rotates the operating unit 704, thereby moving the moving tool 703 toward the second projected portion 702B along a shaft direction VB and achieving to clip the pole 499 between the moving tool 703 and the second projected portion 702B.

This enables the three pole clamps 400 to detachably fix the rack 500 and the communication box 520 to the pole 499.

As illustrated in FIGS. 20A and 20B, the fixing tool 702 has a substantially C-shape, and a first contacting portion 720 is formed on an inner surface of the second projected portion 702B. Further, a second contacting portion 730 is formed inside the moving tool 703, and the first contacting portion 720 and second contacting portion 730 have substantially a C-shape or an arc-shape and face each other in order to surely clamp an outer peripheral portion of the pole 499 from both sides. When the first contacting portion 720 and second contacting portion 730 contact the outer periphery of the pole 499 and are pushed against the same, the pole clamp 400 clips and clamps the pole 499.

As illustrated in FIG. 20A, the first contacting portion 720 includes an outer projected portion 721, a plurality of stepped portions 722, and an inner projected portion 723. In the same manner, the second contacting portion 730 includes an outer projected portion 731, a plurality of stepped portions 732, an inner projected portion 733, and a guide projected portion 734.

As illustrated in FIG. 20A, the shaft direction VB of the operating unit 704 is set inclined at a predetermined angle DG with respect to the X-direction. The angle DG is, for example, about 15 degrees, but not limited thereto. With this configuration, the medical staff moves the rack 500 and communication box 520 toward the pole 499 along the Y1-direction in order to attach the two pole clamps 400 of the rack 500 and the pole clamp 420 of the communication box 520 to the pole 499. In other words, when the pole 499 is passed between the outer projected portion 721 of the first contacting portion 720 and the outer projected portion 731 of the second contacting portion 730 and inserted between the first contacting portion 720 and the second contacting portion 730, presence of the outer projected portion 721 of the first contacting portion 720 and the outer projected portion 731 of the second contacting portion 730 is disposed not to interrupt the pole 499. Therefore, the pole 499 can be smoothly inserted without interruption of the outer projected portion 721 of the first contacting portion 720 and the outer projected portion 731 of the second contacting portion 730 when the pole 499 is passed in the Y1-direction.

In contrast, FIGS. 21A and 21B are diagrams illustrating a mounting configuration of the pole clamp 2400 generally applied as a comparative example of the pole clamp 400 according to the embodiment of the present invention.

As illustrated in FIG. 21A, a pole clamp 2400 is mounted in parallel to a rear surface portion of a rack 2401, and therefore a moving direction of an operating unit 2406 is parallel to the rear surface portion of the rack 2401. An outer projected portion 2404 at a contacting portion 2402 of a moving tool 2398 and an outer projected portion 2405 at a contacting portion 2403 of a projected portion 2399 are projected facing each other in a direction along X-direction. Therefore, as illustrated in FIGS. 21A and 21B, when the medical staff tries to move the rack 2401 close to the pole 499 in the Y1-direction to pass the pole 499 between the outer projected portion 2404 of the contacting portion 2402 and the outer projected portion 2405 of the contacting portion 2403, the outer projected portion 2404 of the contacting portion 2402 and the outer projected portion 2405 of the contacting portion 2403 hit an outer peripheral portion of the pole 499. By this, the pole 499 is pushed by the outer projected portion 2404 of the contacting portion 2402 of the moving tool 2398 and the outer projected portion 2405 of the contacting portion 2403 of the second projected portion 2399, and the pole 499 may be moved backward. When the pole 499 is thus moved, the pole 499 cannot be properly passed between the outer projected portion 2404 and the outer projected portion 2405.

Therefore, as illustrated in FIG. 21B, when the medical staff attaches the rack 2401 smoothly to the pole 499 in the Y1-direction, the medical staff preliminarily needs to move the moving tool 2398 in X2-direction by rotating the operating unit 2406 beforehand and expand a distance DD1 between the outer projected portion 2404 and the outer projected portion 2405 illustrated in FIG. 21A to a distance DD2 illustrated in FIG. 21B. However, in the case of thus expanding the distance between the outer projected portion 2404 and the outer projected portion 2405 to the distance DD2, the rack 2401 cannot be clamped to the pole 499 unless the medical staff rotates again the operating unit 2406 after inserting the pole 499 between the outer projected portion 2404 and the outer projected portion 2405 to put back the outer projected portion 2404 at the contacting portion 2402 of the moving tool 2398 in the X1-direction by the expanded amount from the distance DD1 to the distance DD2 with respect to the outer projected portion 2405 at the contacting portion 2403 of the projected portion 2399. Accordingly, some extra time is spent for the medical staff to mount the rack 2401 to the pole 499. Particularly, in the case where there are many pole clamps preliminarily mounted on the rack and communication box, such extra work time is additionally increased.

In the rack 500 according to the embodiment of the present invention illustrated in FIGS. 20A and 20B, the first contacting portion 720 and second contacting portion 730 can be engaged with the outer peripheral portion of the pole 499 in a short time by the medical staff manually rotating the operating unit 704 to push the moving tool 703 against the pole 499 after the medical staff positions the first contacting portion 720 and second contacting portion 730 so as to face the outer peripheral portion of the pole 499. The rack 500 can be easily clamped to the pole 499 in a short time. Therefore, the medical staff can easily fix the rack 500 and communication box 520 to the pole 499 and detach the rack 500 and communication box 520 from the pole 499 by using the plurality of pole clamps 400.

Figure 22A:
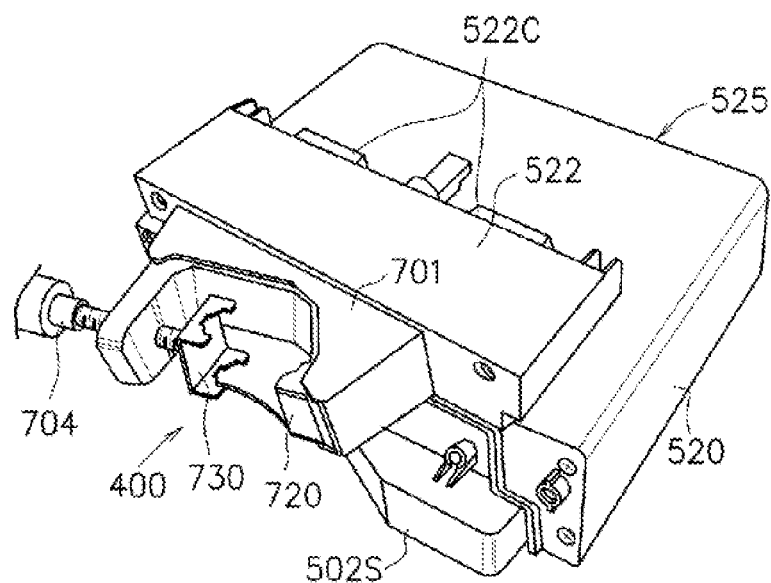
FIG. 22A is a perspective view of the communication box obliquely viewed from the rear side.
Figure 22B:
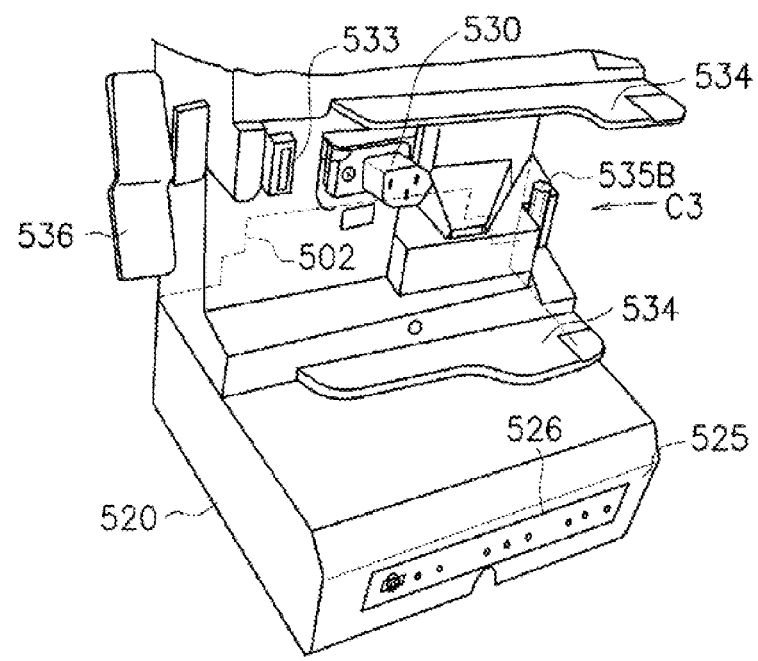
FIG. 22B is a front side perspective view illustrating a state in which the communication box is detachably mounted on a lower portion of the rack.

Next, an example in which the communication box 520 illustrated in FIG. 5 is mounted on an upper portion and a lower portion of the rack 500 will be described with reference to FIGS. 22A, 22B and 23A to 23C. FIG. 22A is a perspective view of the communication box 520 obliquely viewed from the rear side, and FIG. 22B is a perspective view illustrating a state in which the communication box 520 is detachably mounted on the lower connection-receiving portion 540 of the rack 500. FIG. 23A is a perspective view illustrating the lower connection-receiving portion 540 of the rack 500 and the rear surface portion side of the communication box 520 mounted on the lower connection-receiving portion 540. FIG. 23B is a rear perspective view illustrating the rear surface portion side of the communication box 520. FIG. 23C is a rear perspective view illustrating the rear surface portion side of the communication box 520 shown without an inlet box 502S for additional AC power supply.

As illustrated in FIG. 22A, the above-described pole clamp 400 is mounted on the rear surface portion of the communication box 520. The communication box 520 can be, as exemplified in FIG. 4A, detachably mounted on the upper connecting portion 502 of the rack 500 illustrated in FIG. 3. Further, as exemplified in FIGS. 22B and 23A, the communication box 520 can be also detachably mounted on the lower connection-receiving portion 540 of the rack 500.

Thus, depending on necessity, the medical staff can mount the communication box 520 on one or both of the upper connecting portion 502 of the rack 500 and the lower connection-receiving portion 540. Additionally, as illustrated in FIGS. 23A to 23C, a recessed portion 590 for connection is provided at a position below the pole clamp 400 at the rear surface of the communication box 520. The inlet box 502S for additional AC power supply can be further detachably mounted on the recessed portion 590 for connection, for example.

The communication box 520 illustrated in FIGS. 22A and 22B can exchange information with the external computer from the infusion pump 1 mounted on the rack 500 or the syringe pump 1001. For instance, the infusion pump 1 or syringe pump 1001 selects medicine information to be used from the medicine library of the external computer via the communication box 520, and the infusion pump 1 or syringe pump 1001 feeds the medicine based on the selected medicine information. The medicine library is medicine information which is the medicine administration setting group containing the preliminarily registered medicines in the medicine library database (DB). The medical staff can select and set the medicine with the infusion pump 1 or syringe pump 1001 by using the medicine library without executing complex administration setting every time.

Figure 24:
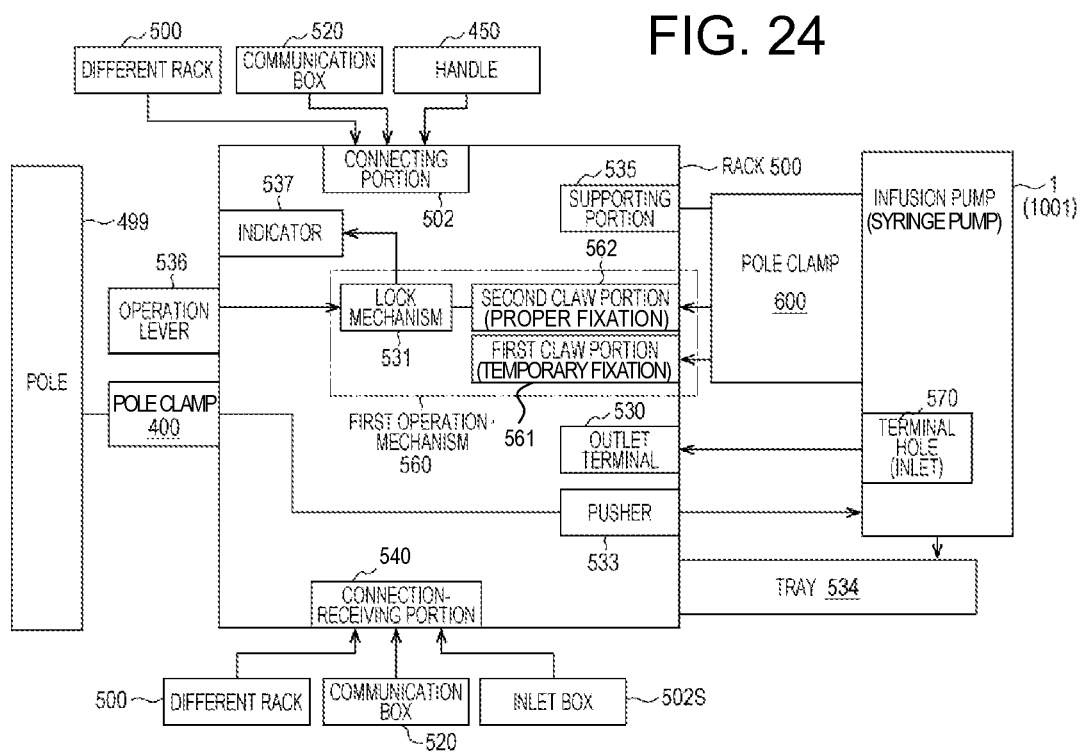
FIG. 24 is a block diagram illustrating a mechanical connecting relation between the rack illustrated in FIG. 5, a pole, and the infusion pump (or syringe pump).

FIG. 24 is a block diagram illustrating a mechanical connecting relation between the above-described rack 500 illustrated in FIG. 5, pole 499, and infusion pump 1 (or syringe pump 1001).

As illustrated in FIG. 24, the rack 500 is detachably fixed to the pole 499 by using the plurality of pole clamps 400. The plurality of infusion pumps 1 or syringe pumps 1001 is detachably fixed to the rack 500 by using the supporting portion 535, pole clamp 600, and lock mechanism 531.

The communication box 520 or the lower connection-receiving portion 540 of the different rack 500 can be detachably mounted on the upper connecting portion 502 of the rack 500. In the same manner, the connecting portion 522 of the communication box 520 or the upper connecting portion 502 of the different rack 500 can be detachably mounted on the lower connection-receiving portion 540 of the rack 500. For example, nine sets of the mounting sections C1 to C3 can be stacked by respectively connecting the different racks 500 to the upper connecting portion 502 and lower connection-receiving portion 540 of the rack 500. Therefore, the infusion pumps 1 or syringe pumps 1001 can be optionally mounted on the nine sets of mounting sections C1 to C3.

Next, a use of the above-described rack 500 will be described.

First, the medical staff places the pole 499 illustrated in FIG. 1 on the floor surface FW and attaches one rack 500 to the pole 499 by using the plurality of pole clamps 400. The infusion pump 1 or syringe pump 1001 has not been mounted on the first mounting section C1 to the third mounting section C3 of the rack 500 yet.

As illustrated in FIGS. 20A and 20B, the shaft direction VB of the operating unit 704 is set inclined at the predetermined angle DG with respect to the X-direction. Therefore, at the time of passing the pole 499 between the outer projected portion 721 of the first contacting portion 720 and the outer projected portion 731 of the second contacting portion 730 along the Y1-direction to be placed between the first contacting portion 720 and the second contacting portion 730, presence of the outer projected portion 721 of the first contacting portion 720 and the outer projected portion 731 of the second contacting portion 730 does not hit the pole 499 and does not interrupt attachment work in which the rack 500 is carried straightly close to the pole 499 along the Y1-direction to pass the pole 499.

In this manner, as for the rack 500, the medical staff manually rotates the operating unit 704 after the first contacting portion 720 and second contacting portion 730 are placed by the medical staff so as to face the outer peripheral portion of the pole 499, thereby pushing the moving tool 703 against the pole 499. By this, the first contacting portion 720 and second contacting portion 730 can be engaged with the outer peripheral portion of the pole 499. The rack 500 can be easily clamped to the pole 499 in a short time. Therefore, the medical staff can easily and surely fix the rack 500 to the pole 499 by using the plurality of pole clamps 400 in a short time.

Next, the medical staff mounts the infusion pumps 1 to the first mounting section C1 and second mounting section C2, and the syringe pump 1001 to the third mounting section C3, for example, as illustrated in FIG. 1. More specifically, as illustrated in FIG. 18A, the medical staff places the lower portion of the infusion pump 1 on the tray 534 while holding the right side of the infusion pump 1 with the right hand and also the left side of the infusion pump 1 with the left hand. By thus placing the lower portion of the infusion pump 1 on the tray 534, subsequent mounting work executed by rotating the infusion pump 1 can be reliably performed without anxiety of dropping the infusion pump 1.

As illustrated in FIG. 18A, the upper post 535A is fitted into the first insertion hole 611 on the infusion pump 1 side and the lower post 535B is fitted into the second insertion hole 612 on the infusion pump 1 side. In this state, the outlet receiving portion 570 of the infusion pump 1 preliminarily faces the outlet terminal 530 on the first mounting section C1 side. The outlet receiving portion 570 thus preliminarily faces the outlet terminal 530 because the outlet terminal 530 is disposed in a projecting manner in the CLC-direction at the predetermined inclination angle θ with respect to the Y2-direction (front-rear direction) of the rack 500 by force of the spring 552 as illustrated in FIG. 12. This causes the outlet receiving portion 570 to directly face the outlet terminal 530.

As illustrated in FIGS. 18A and 18B, the medical staff only rotates the infusion pump 1 around the rotary center shaft CL of the upper post 535A and lower post 535B in the SS-direction with the left hand while holding the left-side portion of the pump with the left hand, thereby surely and smoothly fitting the outlet terminal 530 of the first mounting section C1 side into the outlet receiving portion 570 of the infusion pump 1 for electrical and mechanical connection. Note that mounting work for the infusion pump 1 to the second mounting section C2 and mounting work for the syringe pump 1001 to the third mounting section C3 are executed in the same manner as mounting work for the infusion pump 1 to the first mounting section C1 described above.

As illustrated in FIGS. 18A and 18B, in the case of mounting the infusion pump 1 to the first mounting section C1 of the rack 500 by rotating the pump around the rotary center shaft CL in the SS-direction while the medical staff holds the infusion pump 1 including the pole clamp 600 illustrated in FIGS. 15A and 15B, the tip 561F of the first claw portion 561 is moved to the first stepped portion 621 as illustrated in FIG. 16A and engaged first with the first stepped portion 621 as illustrated in FIGS. 16B and 16C.

In this manner, the infusion pump 1 can be temporarily fixed by engagement of the tip 561F of the first claw portion 561 with the first stepped portion 621 as illustrated in FIGS.

16B and 16C. Therefore, the tip 561F of the first claw portion 561 is necessarily engaged with the first stepped portion 621 even when rotation of the infusion pump 1 in the SS-direction is insufficient and rotation in the SS-direction is stopped in a halfway when the medical staff mounts the infusion pump 1 to the first mounting section C1 of the rack 500 by rotating the infusion pump 1 around the rotary center shaft CL in the SS-direction. Therefore, it is possible to prevent the infusion pump 1 from falling from the first mounting section C1.

As illustrated in FIGS. 16B and 16C, while the infusion pump 1 is temporarily fixed, the red region 641R of the slide plate 641 is displayed at the window 650 of the indicator 537 illustrated in FIG. 19B. This enables the medical staff to visually confirm that the infusion pump 1 (or syringe pump 1001) is temporarily fixed to the rack 500 by checking the color displayed at the indicator 537, which is effective in a safety aspect.

Additionally, as illustrated in FIGS. 16B and 16C, while the medical staff further rotates the infusion pump around the rotary center shaft CL in the SS-direction while holding the infusion pump 1 and the pole clamp 600 illustrated in FIGS. 15A and 15B, the second claw portion 562 is engaged with the second stepped portion 622 as illustrated in FIGS. 17A and 17B. In this manner, as for the infusion pump 1, the infusion pump 1 (or syringe pump 1001) is properly fixed to the rack 500 by the tip 562F of the second claw portion 562 being engaged with the second stepped portion 622. As for the tip 562F of the second claw portion 562 and the second stepped portion 622, the tip 562F of the second claw portion 562 is not lifted from the second stepped portion 622 even when the pole clamp 600 is pulled in the SS1-direction together with the infusion pump 1. In other words, because the infusion pump 1 cannot be taken out in the SS1-direction while the infusion pump 1 is properly fixed, the infusion pump 1 (or syringe pump 1001) can be prevented from falling, which is effective in a safety aspect.

As illustrated in FIGS. 15A and 15B, the opening portion 611A of the first insertion hole 611 and the opening portion 612A of the second insertion hole 612 are formed opened in the X2-direction. Therefore, as illustrated in FIG. 18B, when the infusion pump 1 (or syringe pump 1001) is properly fixed to the first mounting section C1 (second mounting section C2 or third mounting section C3), the upper post 535A is prevented from being detached from the first insertion hole 611 on the infusion pump 1 (or syringe pump 1001) side, and the lower post 535B is prevented from being detached from the second insertion hole 612 on the infusion pump 1 (or syringe pump 1001) side.

When the infusion pump 1 (or syringe pump 1001) is thus fixed to the first mounting section C1 (second mounting section C2 or the third mounting section C3), the infusion pump 1 (or syringe pump 1001) can be safely and surely fixed to the first mounting section C1 (second mounting section C2 or third mounting section C3) by using the upper post 535A and lower post 535B of the supporting portion 535, the lock mechanism 531, and the outlet terminal 530.

When the infusion pump 1 is properly fixed, the blue region 641B of the slide plate 641 which is a color region different from the color (red color) region indicating the temporary fix state is displayed at the window 650 of the indicator 537 illustrated in FIG. 19B. By this, it can be visually confirmed that the infusion pump 1 is properly fixed.

Meanwhile, as illustrated in FIG. 22A, the communication box 520 can be detachably mounted, as exemplified in FIG. 4A, to the upper connecting portion 502 of the rack 500 illustrated in FIG. 3. Further, as exemplified in FIGS. 22B and 23A, the communication box 520 can be also detachably mounted on the lower connection-receiving portion 540 of the rack 500. Therefore, the medical staff can attach the communication box 520 to at least one of the upper portion and the lower portion of the rack 500, depending on necessity.

Next, an operation at the time of detaching the mounted infusion pump 1 (or syringe pump 1001) from the mounting section C1 to the third mounting section C3 of the rack 500 as illustrated in FIG. 1 will be described.

When the medical staff rotates the operation lever 536 illustrated in FIGS. 11 and 13A in the RL-direction by a predetermined angle θ1, the second claw portion 562 for proper fixation of the lock mechanism 531 is lifted in the DF-direction as illustrated in FIGS. 17A and 17B. Therefore, engagement between the second claw portion 562 and the second stepped portion 622 of the engagement portion 620 is released, and the proper fixing state of the infusion pump 1 (or syringe pump 1001) is released. However, as illustrated in FIGS. 16B and 16C, the temporary fixing state between the first claw portion 561 and the first stepped portion 621 of the engagement portion 620 is not released.

When the medical staff rotates the operation lever 536 illustrated in FIG. 11 in the RL-direction up to the predetermined angle θ2 illustrated in FIG. 13B in this state, the tip 533A of the pusher 533 illustrated in FIG. 13B pushes the rear surface portion side of the infusion pump 1 (or syringe pump 1001) by the amount of predetermined stroke STC in the Y2-direction. By this, the pusher 533 forcibly pushes the rear surface portion of the infusion pump 1 (or syringe pump 1001) in the SS1-direction illustrated in FIGS. 16B and 16C. When the rear surface portion of the infusion pump 1 (or syringe pump 1001) is pushed in the SS1-direction, the first claw portion 561 is lifted from the first stepped portion 621 of the engagement portion 620 and the temporary fixing state of the infusion pump 1 (or syringe pump 1001) can be released.

As described above, the infusion pump 1 can be detached by being released from the proper fixing state illustrated in FIGS. 17A and 17B after being released from the temporary fixing state as illustrated in FIGS. 16A to 16C. When the infusion pump 1 is detached by thus being rotated in the SS1-direction, the lower portion of the infusion pump 1 is placed on the tray 534 illustrated in FIG. 10A. Therefore, the infusion pump 1 is prevented from falling unexpectedly.

After that, the medical staff holds the left-side portion of the infusion pump 1 with the left hand and the right-side portion of the infusion pump 1 with the right hand, and detaches the upper post 535A from the first insertion hole 611 on the infusion pump 1 side illustrated in FIGS. 15A and 15B, and further detaches the lower post 535B from the second insertion hole 612 on the infusion pump 1 side. In this manner, the medical staff can easily and safely detach the infusion pump 1 (or syringe pump 1001).

The above-described mounting work for the infusion pump 1 to the first mounting section C1 to the third mounting section C3 of the rack 500 is same as the mounting work for the syringe pump 1001 to the first mounting section C1 to the third mounting section C3 of the rack 500.

As illustrated in FIGS. 18A and 18B, the medical device rack 500 according to the embodiment of the present invention includes the main body 501, and the mounting sections C1, C2, C3 provided at the main body 501 for detachably mounting the medical device used in a posture oriented in the lateral direction. The mounting sections C1, C2, C3 each include the supporting portion 535 that rotatably supports the medical device by being fitted to the medical device side. With this configuration, the supporting portion 535 of each of the mounting sections C1, C2, C3 can support the medical device in a rotatable manner, and therefore the medical staff can mount the medical device to each of the mounting section C1, C2, C3. Further, in the case where the medical staff detaches the medical devices from each of the mounting sections C1, C2, C3, the medical devices are partly supported by the supporting portion 535 and the medical staff can detach the medical device from each of the mounting sections C1, C2, C3 while rotating the medical device with one hand. In other words, the medical staff can easily and surely mount and detach the medical device because the medical device can be mounted on and detached from the rack without constantly holding the relatively heavy medical device with both hands.

As illustrated in FIG. 2, the plurality of mounting sections C1, C2, C3 is arranged in the vertical direction (Z-direction) of the rack 500, and each of the mounting sections C1, C2, C3 includes the upper wall CW1 positioned on the upper portion side of the medical device to be mounted and the lower wall CV1 positioned on the lower portion side of the medical device. The supporting portion 535 includes the upper post 535A projected downward from the upper wall CW1 and detachably fitted to the rear surface portion side of the medical device, and the lower post 535B projected upward from the lower wall CV1, facing the upper post 535A, and detachably fitted to the rear surface portion side of the medical device. With this configuration, the upper post 535A and lower post 535B of the supporting portion 535 are fitted to the rear surface portion side of the medical device, thereby supporting the medical device in a rotatable manner. Therefore, despite such a simple configuration, in the case of mounting the medical device to each of the mounting sections C1, C2, C3 or detaching the medical device from each of the mounting sections C1, C2, C3, the medical device is partly supported by the supporting portions 535 and the medical device can be mounted on each of the mounting sections C1, C2, C3, or the medical device can be detached from each of the mounting sections C1, C2, C3 in reverse while the medical device is rotated with one hand.

The mounting sections C1, C2, C3 each include the lock mechanism 531 whereby the medical device can be detachably fixed to each of the mounting sections C1, C2, C3 by being engaged with the rear surface portion side of the medical device as illustrated in FIGS. 10A and 10B. Therefore, because the lock mechanism 531 is engaged with the rear surface portion side of the medical device positioned at each of the mounting sections C1, C2, C3, the medical device can be surely and mechanically locked and fixed safely to each of the mounting sections C1, C2, C3.

As illustrated in FIG. 10A, the tray 534 is provided on the lower wall CV1 as the supporting projected portion that supports the lower portion of the medical device. Therefore, the tray 534 can support the lower portion of the medical device when the medical device is mounted on each of the mounting sections C1, C2, C3 by being rotated around the supporting portion 535 and the medical device is detached from each of the mounting sections C1, C2, C3 by being rotated around the supporting portion 535. Therefore, the relatively heavy medical device can be safely mounted and detached.

As illustrated in FIGS. 18A and 18B, the outlet terminal 530 is provided at each of the mounting sections C1, C2, C3, and electrically connects the medical device with the rack 500 by being inserted into the outlet receiving portion 570 provided at the medical device when the medical device is mounted on each of the mounting sections C1, C2, C3. The outlet terminal 530 is disposed in each of the mounting sections C1, C2, C3 along the rotary direction (CLC-direction) of the outlet receiving portion 570 around the supporting portion 535. Therefore, when the medical device is rotated around the supporting portion 535 to be mounted on each of the mounting sections C1, C2, C3, the outlet receiving portion 570 on the medical device side can be surely connected to the outlet terminal 530 on each of the mounting sections C1, C2, C3 sides.

The outlet terminal 530 includes the spring 552 which is an energizing member disposed in the rotary direction around the supporting portion 535 in each of the mounting sections C1, C2, C3. When the medical device is mounted on each of the mounting sections C1, C2, C3, the outlet terminal 530 is fitted into the outlet receiving portion 570 by being pushed in the rotary direction around the supporting portion 535 against the force of the spring 552. Therefore, when the medical device is rotated around the supporting portion 535 to be mounted on each of the mounting sections C1, C2, C3, the outlet terminal 530 on each of the mounting sections C1, C2, C3 sides can be surely connected to the outlet receiving portion 570 on the medical device side by utilizing the force of the spring 552. Further, when the medical device is rotated around the supporting portion 535 to be detached from each of the mounting sections C1, C2, C3, the outlet terminal 530 on each of the mounting sections C1, C2, C3 sides can be returned again in the rotary direction (CLC-direction) around the supporting portion 535 by utilizing the force of the spring 552.

The supporting portion 535 is detachably fitted to the pole clamp 600 for mounting the medical device to the pole 499. Therefore, the supporting portion 535 on each of the mounting sections C1, C2, C3 sides can detachably support the medical device by utilizing the pole clamp 600 on the medical device side.

The present invention is not limited to the above-described embodiment, and various changes can be made without departing from the scope of claims.

The infusion tube 200 illustrated in FIGS. 8A and 8B or the syringe 1200 illustrated in FIG. 9 are disposed in the tube mounting section 50 or the syringe setting portion 1006 in the horizontal direction (X-direction), and the right side thereof is the upstream side of a liquid medicine and the left side thereof is the downstream side of the liquid medicine. However, not limited thereto, the infusion tube 200 illustrated in FIGS. 8A and 8B and the syringe 1200 illustrated in FIG. 9 may be disposed with the upstream side thereof positioned slightly upside and the downstream side thereof positioned slightly downside although the pumps are to be laterally disposed. According to the present invention, the lateral direction in which the infusion tube 200 illustrated in FIGS. 8A and 8B and the syringe 1200 illustrated in FIG. 9 are disposed also includes a horizontal direction and a direction slightly inclined with respect to the horizontal direction.

The medical device is not limited to the infusion pump 1 and the syringe pump 1001 but may be other kinds of medical devices, too.

The rack 500 illustrated includes the mounting sections C1, C2, C3, but is not limited thereto, and may be configured to include two mounting sections or four or more mounting sections.

The components of the above-described embodiments can be partly omitted or can be optionally combined in a manner different from the above embodiment.

What is claimed is:

1. A system comprising:
an infusion pump comprising:
a main body case,
a display unit,
an operation panel,
a tube mounting section configured for mounting an infusion tube, and
an access cover configured to cover the tube mounting section,
wherein the display unit and the operation panel are disposed at an upper portion of the main body case, and
wherein the tube mounting section and the access cover are disposed at a lower portion of the main body case; and
a medical device rack in which the infusion pump is detachably mountable, the medical device rack comprising:
a main body; and
a mounting section provided in the main body, the mounting section being configured such that the infusion pump is detachably mountable in a posture oriented in a lateral direction,
wherein the mounting section comprises:
an upper wall configured to be positioned on an upper side of the infusion pump,
a lower wall configured to be positioned on a lower portion side of the infusion pump, and
a supporting portion configured to be detachably fitted to the infusion pump to support the infusion pump in a rotatable manner, and
wherein the supporting portion comprises:
an upper post extending downward from the upper wall and configured to be detachably fitted into a first insertion hole located on a rear surface portion side of the infusion pump, and
a lower post extending upward from the lower wall and configured to be detachably fitted into a second insertion hole located on the rear surface portion side of the infusion pump,
wherein the upper post and the lower post face each other along a same axis.

2. The system according to claim 1, wherein the mounting section includes a lock mechanism configured to detachably fix the infusion pump to the mounting section by being engaged to a rear surface portion side of the infusion pump.

3. The system according to claim 1, wherein the lower wall includes a supporting projected portion configured to support a lower portion of the infusion pump.

4. The system according to claim 1, wherein the mounting section includes an outlet terminal configured to electrically connect the infusion pump with the rack by being inserted into an outlet receiving portion of the infusion pump when the infusion pump is mounted on the mounting section, and wherein the outlet terminal is disposed in the mounting section and configured such that, when the infusion pump is mounted on the mounting section, the outlet terminal is aligned with the outlet receiving portion of the infusion pump along a rotary direction of the outlet receiving portion of the infusion pump around the supporting portion.

5. The system according to claim 4, wherein the outlet terminal includes an energizing member, and the mounting section is configured such that, when the infusion pump is mounted on the mounting section, the outlet terminal is fitted into the outlet receiving portion by being pushed in a rotary direction around the supporting portion against the force of the energizing member.

6. The system according to claim 1, wherein the supporting portion is configured to be detachably fitted to a pole clamp member configured to mount the infusion pump to a pole.

7. A medical device rack in which a plurality of medical devices are detachably mountable, the medical device rack comprising:
a main body; and
a plurality of mounting sections provided in the main body, each mounting sections being configured such that a respective medical device is detachably mountable in a posture oriented in a lateral direction,
wherein each mounting section comprises:
an upper wall configured to be positioned on an upper side of the medical device,
a lower wall configured to be positioned on a lower portion side of the medical device, and
a supporting portion configured to be detachably fitted to the respective medical device to support the respective medical device in a rotatable manner, and
wherein each supporting portion comprises:
an upper post extending downward from the upper wall and configured to be detachably fitted into a first insertion hole located on a rear surface portion side of the medical device, and
a lower post extending upward from the lower wall and configured to be detachably fitted into a second insertion hole located on the rear surface portion side of the medical device,
wherein the upper post and the lower post face each other along a same axis.

8. The medical device rack according to claim 7, wherein each mounting section includes a lock mechanism configured to detachably fix the respective medical device to the respective mounting section by being engaged to a rear surface portion side of the respective medical device.

9. The medical device rack according to claim 7, wherein each lower wall includes a supporting projected portion configured to support a lower portion of the respective medical device.

10. The medical device rack according to claim 7, wherein each mounting section includes an outlet terminal configured to electrically connect the respective medical device with the rack by being inserted into an outlet receiving portion of the respective medical device when the respective medical device is mounted on the mounting section, and wherein the outlet terminal is disposed in the mounting section and configured such that, when the respective medical device is mounted on the mounting section, the outlet terminal is aligned with the outlet receiving portion of the respective medical device along a rotary direction of the outlet receiving portion of the respective medical device around the supporting portion.

11. The medical device rack according to claim 10, wherein each outlet terminal includes an energizing member, and each mounting section is configured such that, when the respective medical device is mounted on the mounting section, the respective outlet terminal is fitted into the respective outlet receiving portion by being pushed in a rotary direction around the respective supporting portion against the force of the respective energizing member.

12. The medical device rack according to claim 7, wherein each of the supporting portions is configured to be detachably fitted to a pole clamp member, each pole clamp member being configured to mount the respective medical device to a pole.

13. The medical device rack according to claim 7, wherein at least one of the medical devices is an infusion pump that comprises:
   a main body case;
   a display unit;
   an operation panel;
   a tube mounting section configured to mount an infusion tube for feeding a medicine; and
   an access cover configured to cover the tube mounting section,
   wherein the display unit and the operation panel are disposed at an upper portion of the main body case, and
   wherein the tube mounting section and the access cover are disposed at a lower portion of the main body case.

14. The medical device rack according to claim 7, wherein at least one of the medical devices is a syringe pump that comprises:
   a main body case;
   a display unit;
   an operation panel; and
   a syringe mounting section configured to mount a syringe for feeding a medicine,
   wherein the display unit and the operation panel are disposed at an upper portion of the main body case, and
   wherein the syringe mounting section is disposed at a lower portion of the main body case.

15. A system comprising:
   a syringe pump comprising:
      a main body case,
      a display unit,
      an operation panel, and
      a syringe mounting section configured for mounting a syringe,
      wherein the display unit and the operation panel are disposed at an upper portion of the main body case, and
      wherein the syringe mounting section is disposed at a lower portion of the main body case; and
   a medical device rack in which the syringe pump is detachably mountable,
      a main body; and
      a mounting section provided in the main body, the mounting section being configured such that the syringe pump is detachably mountable in a posture oriented in a lateral direction,
   wherein the mounting section comprises:
      an upper wall configured to be positioned on an upper side of the syringe pump,
      a lower wall configured to be positioned on a lower portion side of the syringe pump, and
      a supporting portion configured to be detachably fitted to the syringe pump to support the syringe pump in a rotatable manner, and
   wherein the supporting portion comprises:
      an upper post extending downward from the upper wall and configured to be detachably fitted into a first insertion hole located on a rear surface portion side of the syringe pump, and
      a lower post extending upward from the lower wall and configured to be detachably fitted into a second insertion hole located on the rear surface portion side of the syringe pump,
      wherein the upper post and the lower post face each other along a same axis.

16. The system according to claim 15, wherein the mounting section includes a lock mechanism configured to detachably fix the syringe pump to the mounting section by being engaged to a rear surface portion side of the syringe pump.

17. The system according to claim 15, wherein the lower wall includes a supporting projected portion configured to support a lower portion of the syringe pump.

18. The system according to claim 15, wherein the mounting section includes an outlet terminal configured to electrically connect the syringe pump with the rack by being inserted into an outlet receiving portion of the syringe pump when the syringe pump is mounted on the mounting section, and wherein the outlet terminal is disposed in the mounting section and configured such that, when the syringe pump is mounted on the mounting section, the outlet terminal is aligned with the outlet receiving portion of the syringe pump along a rotary direction of the outlet receiving portion of the syringe pump around the supporting portion.

19. The system according to claim 18, wherein the outlet terminal includes an energizing member, and the mounting section is configured such that, when the syringe pump is mounted on the mounting section, the outlet terminal is fitted into the outlet receiving portion by being pushed in a rotary direction around the supporting portion against the force of the energizing member.

20. The system according to claim 15, wherein the supporting portion is configured to be detachably fitted to a pole clamp member configured to mount the syringe pump to a pole.

* * * * *